United States Patent
Nishimura et al.

(10) Patent No.: US 10,866,436 B2
(45) Date of Patent: Dec. 15, 2020

(54) EYEGLASSES PROTECTION DEVICE

(71) Applicant: DEXERIALS CORPORATION, Tokyo (JP)

(72) Inventors: Kimitaka Nishimura, Tokyo (JP); Satoshi Kawamura, Tokyo (JP)

(73) Assignee: DEXERIALS CORPORATION, Tokyo (JP)

(*) Notice: Subject to any disclaimer, the term of this patent is extended or adjusted under 35 U.S.C. 154(b) by 137 days.

(21) Appl. No.: 15/309,355

(22) PCT Filed: May 7, 2015

(86) PCT No.: PCT/JP2015/063225
§ 371 (c)(1),
(2) Date: Nov. 7, 2016

(87) PCT Pub. No.: WO2015/170716
PCT Pub. Date: Nov. 12, 2015

(65) Prior Publication Data
US 2017/0075146 A1 Mar. 16, 2017

(30) Foreign Application Priority Data

May 7, 2014 (JP) ................................. 2014-096125

(51) Int. Cl.
*G02C 7/16* (2006.01)
*G02C 11/00* (2006.01)
(Continued)

(52) U.S. Cl.
CPC ................ *G02C 7/16* (2013.01); *G02B 1/118* (2013.01); *G02C 9/04* (2013.01); *G02C 11/12* (2013.01)

(58) Field of Classification Search
CPC ............. G02C 11/12; A61F 9/04; A61F 9/045
(Continued)

(56) References Cited

U.S. PATENT DOCUMENTS 2,541,242 A * 2/1951 Grove ..................... A61F 9/045
2/13
5,020,533 A 6/1991 Hubbard et al.
(Continued)

FOREIGN PATENT DOCUMENTS

FR 2553905 A1 * 4/1985 ............... G02C 9/00
FR 2692373 A1 * 12/1993 ............. G02C 11/00
(Continued)

OTHER PUBLICATIONS

JP S59-057652 translation; Oct. 2018.*
(Continued)

*Primary Examiner* — Zachary W Wilkes
(74) *Attorney, Agent, or Firm* — Paratus Law Group, PLLC

(57) ABSTRACT

There is provided a novel and improved eyeglasses protection device capable of suppressing occurrence of reflected light that may enter eyes of a user of the eyeglasses protection device and thus reducing fatigue of the user, the eyeglasses protection device including: a lens surface protective part configured to protect a lens surface of eyeglasses. The lens surface protective part is equipped with a substrate film, and a micro concavo-convex structure that is formed on a surface of the substrate film, with an average period of the concavo-convex part being equal to or less than a wavelength of visible light. According to the aforementioned viewpoint of the present invention, it is possible to suppress occurrence of reflected light that may enter eyes of a user of the eyeglasses protection device because the micro concavo-convex structure is formed in the lens surface protective part of the eyeglasses protection device.

16 Claims, 11 Drawing Sheets

(51) Int. Cl.
*G02B 1/118* (2015.01)
*G02C 9/04* (2006.01)

(58) Field of Classification Search
USPC .................................. 351/47; 128/858; 2/13
See application file for complete search history.

(56) References Cited

U.S. PATENT DOCUMENTS

| | | | | |
|---|---|---|---|---|
| 5,206,956 | A | * | 5/1993 | Olson ........................ A61F 9/02 |
| | | | | 128/857 |
| 5,388,269 | A | * | 2/1995 | Griffin .................... A61F 9/045 |
| | | | | 2/13 |
| 5,446,925 | A | | 9/1995 | Baker et al. |
| 5,695,694 | A | * | 12/1997 | Iwata .......................... C08J 5/18 |
| | | | | 264/1.34 |
| 6,582,073 | B1 | * | 6/2003 | Hayes ....................... G02C 7/16 |
| | | | | 2/13 |
| 2010/0323165 | A1 | | 12/2010 | Sakuma et al. |
| 2011/0128629 | A1 | * | 6/2011 | Takahashi .............. G02B 1/118 |
| | | | | 359/601 |
| 2012/0047614 | A1 | | 3/2012 | Choi |
| 2012/0069290 | A1 | | 3/2012 | Phillips |
| 2015/0323704 | A1 | | 11/2015 | Nishimura et al. |

FOREIGN PATENT DOCUMENTS

| | | |
|---|---|---|
| JP | 59-057652 | 4/1984 |
| JP | 03-500497 | 2/1991 |
| JP | 06-029511 | 4/1994 |
| JP | 2939627 | 6/1999 |
| JP | 3079204 | 8/2001 |
| JP | 2005-049669 | 2/2005 |
| JP | 3160039 | 5/2010 |
| JP | 2011-511320 | 4/2011 |
| JP | 2013-195579 | 9/2013 |
| WO | WO89/010106 | 11/1989 |
| WO | WO2008/096872 A1 | 8/2008 |
| WO | WO2014/112555 A1 | 7/2014 |

OTHER PUBLICATIONS

"How to Clean Your Glasses." The Pupil's Lounge, Jul. 2, 2013, blog.39dollarglasses.com/2013/07/how-to-clean-your-glasses/.*
Dec. 18, 2017, European Search Report Issued for related EP application No. 15789805.7.

* cited by examiner

EYEGLASSES PROTECTION DEVICE

CROSS REFERENCE TO PRIOR APPLICATION

This application is a National Stage Patent Application of PCT International Patent Application No. PCT/JP2015/063225 (filed on May 7, 2015) under 35 U.S.C. § 371, which claims priority to Japanese Patent Application No. 2014-096125 (filed on May 7, 2014), which are all hereby incorporated by reference in their entirety.

TECHNICAL FIELD

The present invention relates to an eyeglasses protection device.

BACKGROUND ART

A large number of protection devices for individuals have been used as means for preventing occupational infection in medical service workers. In particular, eye protection devices for preventing exposure to blood and body fluid have been used during examinations and surgeries and have helped prevention of occupational infection by blood borne pathogens (HIV, HBV, HCV).

Patent Literature 1 (Japanese Patent No. 2939627) discloses a face mask and a visor configured with a transparent visor coupled to a mask as an example of an eye protection device as described above. Patent Literature 2 (Japanese Utility Model Registered Publication No. 3160039) discloses an eye-shield configured to be detachably attached to a mask. Patent Literature 3 (Published Japanese Translation No. H3-500497) discloses a face protector with groove holes through which temples of eye glasses are inserted.

CITATION LIST

Patent Literature

Patent Literature 1: JP 2939627B
Patent Literature 2: Japanese Utility Model Registered Publication No. 3160039
Patent Literature 3: JP H3-500497T

SUMMARY OF INVENTION

Technical Problem

However, eye protection devices in the related art do not include any arrangement for preventing reflection of light. Therefore, there is a possibility of a user of such an eye protection device being blinded by reflected light from the surface of the eye protection device. Also, there is a possibility of eyestrain increasing due to the reflected light. Therefore, there is a possibility of the user of the eye protection device feeling fatigue due to the reflected light. In particular, such eye protection devices are used under shadowless lamps in more cases in recent years. Since intensity of the reflected light particularly increases in such cases, fatigue of persons who wear the eye protection devices significantly increases.

Thus, the present invention was made in view of the above problems, and an object of the present invention is to provide a novel and improved eyeglasses protection device capable of suppressing occurrence of reflected light that may enter eyes of a user of the eyeglasses protection device and thus reducing fatigue of the user.

Solution to Problem

In order to solve the above problems, according to a viewpoint of the present invention, there is provided an eyeglasses protection device including: a lens surface protective part configured to protect a lens surface of eyeglasses. The lens surface protective part is equipped with a substrate film, and a micro concavo-convex structure that is formed on a surface of the substrate film, with an average period of the concavo-convex part being equal to or less than a wavelength of visible light.

Here, a plurality of temple protective parts that are formed at both ends of the lens surface protective part in a length direction and protect temples of the eyeglasses may be included. The temple protective parts may be equipped with attachment parts at which the eyeglasses protection device is able to be attached to the temples of the eyeglasses.

The attachment parts may be equipped with a plurality of insertion holes into which the temples of the eyeglasses are inserted. The plurality of insertion holes may be aligned in an insertion direction of the temples.

The attachment parts may be equipped with a traverse cut hole that crosses in an oblique direction between the adjacent insertion holes, and an upper holding part and a lower holding part formed by the plurality of insertion holes and the traverse cut hole.

The traverse cut hole may be formed at one temple protective part among the plurality of temple protective parts.

The attachment parts may be equipped with one or a plurality of auxiliary cut holes that extend from outer edges of the insertion holes toward the outside of the insertion holes, and auxiliary holding parts formed by the auxiliary cut holes in circumferences of the insertion holes.

The micro concavo-convex structure may be formed of a hardened ultraviolet curable resin.

The micro concavo-convex structure may be hydrophilic.

An in-plane retardation value of the lens surface protective part may be equal to or less than 100 nm with respect to the wavelength of the visible light.

According to another viewpoint of the present invention, there is provided an eyeglasses protection device laminated article in which the aforementioned eyeglasses protection devices are laminated.

According to the aforementioned viewpoint of the present invention, it is possible to suppress occurrence of reflected light that may enter eyes of a user of the eyeglasses protection device because the micro concavo-convex structure is formed in the lens surface protective part of the eyeglasses protection device.

Advantageous Effects of Invention

According to the present invention, it is possible to suppress occurrence of reflected light that may enter the eyes of the user of the eyeglasses protection device and thus reduce fatigue of the user as described above.

DESCRIPTION OF EMBODIMENTS

Figure 1:
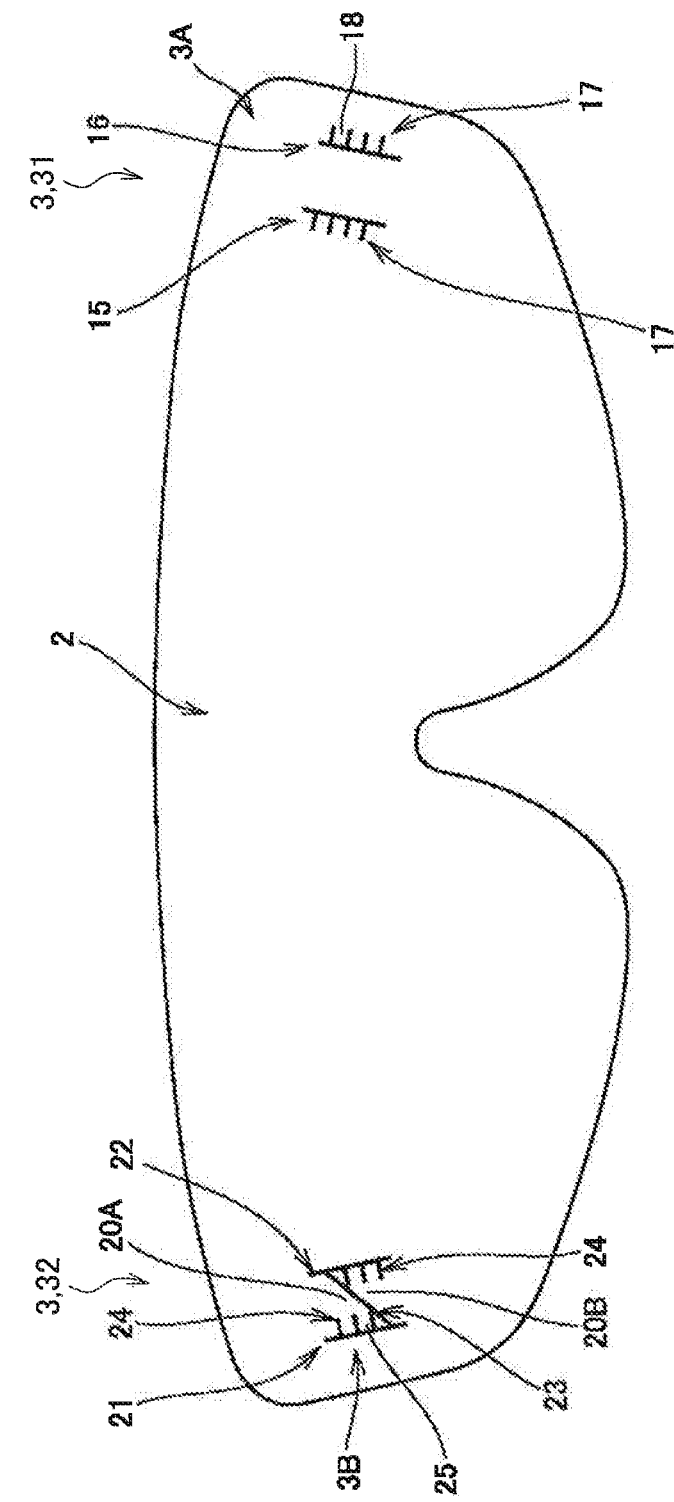
FIG. 1 is a front view illustrating an eyeglasses protection device according to the embodiment.

Hereinafter, (a) preferred embodiment(s) of the present invention will be described in detail with reference to the appended drawings. In this specification and the appended drawings, structural elements that have substantially the same function and structure are denoted with the same reference numerals, and repeated explanation of these structural elements is omitted.

<1. Overall Configuration>

First, an overall configuration of an eyeglasses protection device 1 according to the embodiment will be described based on FIGS. 1 and 2. The eyeglasses protection device 1 is equipped with a lens surface protective part 2 and a plurality of temple protective parts 3. The lens surface protective part 2 protects a lens surface 4a of eyeglasses 4. The temple protective parts 3 are formed at both ends of the lens surface protective part 2 in a length direction and protect temples 5 of the eyeglasses 4. The temple protective parts 3 have attachment parts 3A and 3B. By the attachment parts 3A and 3B, the eyeglasses protection device 1 is attached to the eyeglasses 4 or is detached from the eyeglasses 4. The eyeglasses protection device 1 protects a user of the eyeglasses protection device 1 (hereinafter, also simply referred to as a "user") from various airborne substances (liquid such as blood or body fluid or various aggregated substances, for example) by protecting the lens surface 4a and the temples 5 of the eyeglasses 4.

Here, the type of the eyeglasses 4 to which the eyeglasses protection device 1 is attached is not particularly limited. Examples of the eyeglasses 4 include various correctional eyeglasses, magnifying lenses for surgery (provided with the temples 5), and 3D image eyeglasses. The 3D image eyeglasses may be used for viewing 3D images displayed by various display devices. Here, a 3D image is formed of a right eye image and a left eye image. The right eye image and the left eye image differ from each other. In particular, minimally invasive scopic surgeries are performed more often in recent years. As an endoscopic device for performing endoscopic surgery, a 3D endoscopic device capable of performing stereoscopic observation of a target of treatment has been employed. The 3D endoscopic device displays a 3D image of the target of treatment. As a 3D scheme applied to the 3D endoscopic device, a circular polarization scheme is exemplified. The eyeglasses protection device 1 according to the embodiment can also be applied to eyeglasses used for such a 3D endoscopic device.

<2. Configuration of Lens Surface Protective Part>

Figure 2:
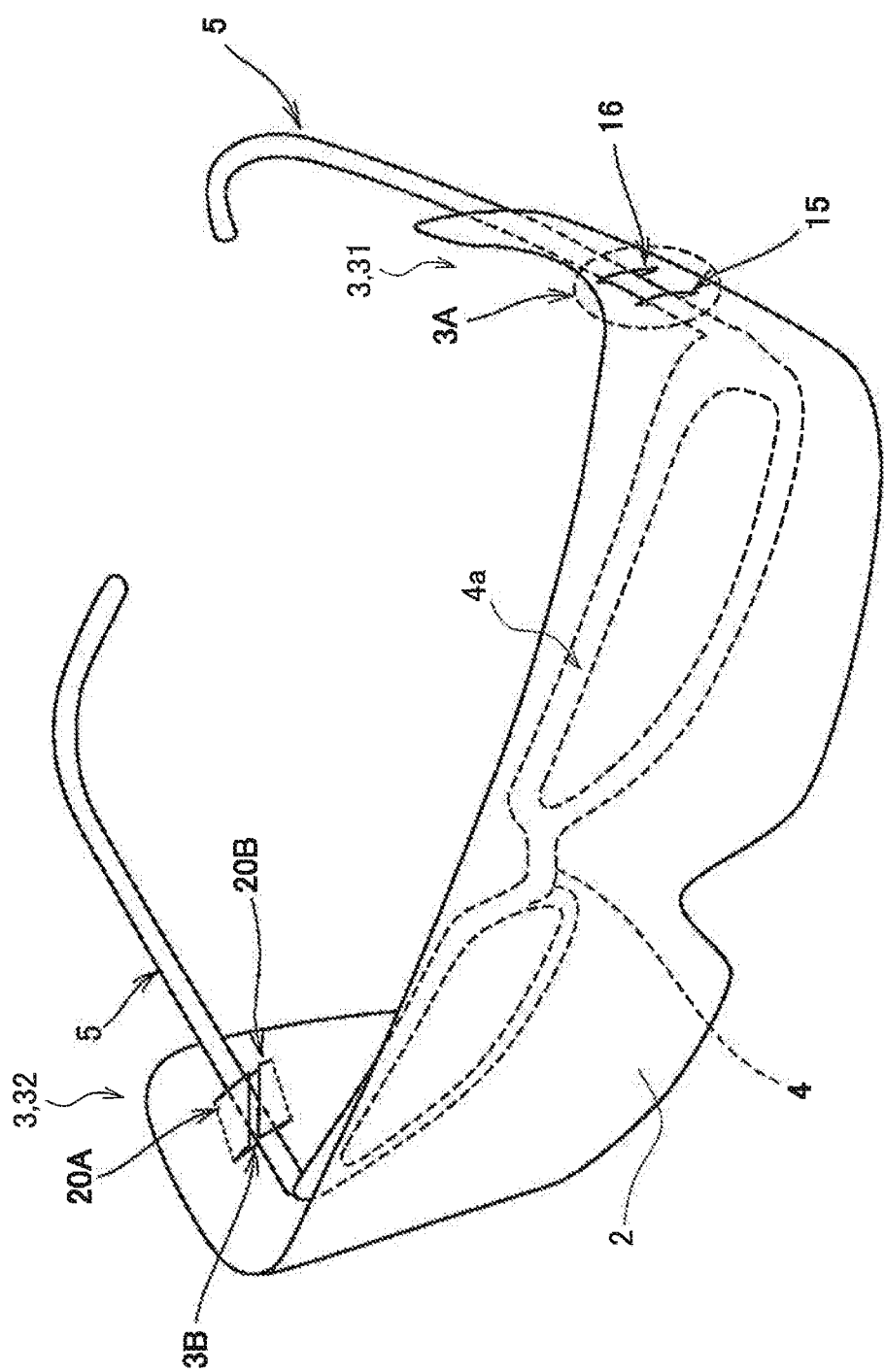
FIG. 2 is a perspective view illustrating a state in which the eyeglasses protection device is attached to eyeglasses.
Figure 3:
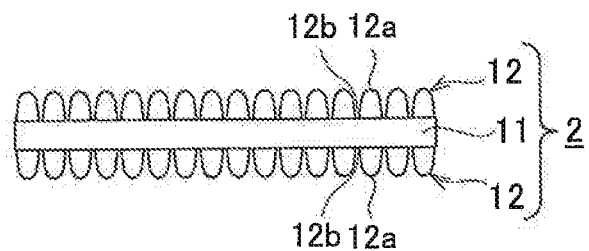
FIG. 3 is sectional view illustrating an example of a lens surface protective part.

Next, a detailed configuration of the lens surface protective part 2 will be described based on FIGS. 1 to 4. The lens surface protective part 2 is a member that protects the lens surface 4a of the eyeglasses 4 as described above. That is, the lens surface protective part 2 is arranged outside the lens surface 4a when the eyeglasses protection device 1 is attached to the eyeglasses 4. The lens surface protective part 2 is preferably wider than the lens surface 4a. The lens surface protective part 2 is equipped with a substrate film 11 and a micro concavo-convex structure 12 as illustrated in FIG. 3.

(2-1. Structure of Substrate Film)

The substrate film 11 is formed of a material that has at least transparency. The material forming the substrate film is not particularly limited as long as the material has transparency. A refractive index of the substrate film 11 is preferably from 1.30 to 2.00, and is preferably from 1.34 to 2.00, for example. The material forming the substrate film preferably has flexibility as well as transparency. As an example of the material forming the substrate film, a plastic material is exemplified.

Although examples of the plastic material that can be applied to the substrate film 11 include methyl methacrylate (co)polymer, polycarbonate, triacetyl cellulose, polyethylene, polyethylene terephthalate, polyethylene naphthalate, polystyrene, styrene (co)polymer, methyl methacrylate-styrene copolymer, polymethyl methacrylate, cellulose diacetate, cellulose triacetate, cellulose acetate butyrate, polyvinyl alcohol, polyester, polyamide, polyimide, polyether sulfone, cycloolefin, polysulfone, polypropylene, polymethylpentene, polyvinyl chloride, polyvinyl acetal, polyether ketone, polyurethane, and glass, the plastic material is not limited thereto.

When the substrate film 11 is formed of the above plastic material, the substrate film 11 is manufactured by a method of stretching the above plastic material or forming a film after diluting the plastic material in a solvent and drying the material.

When the substrate film 11 is formed of the above plastic material, various underlayers may be formed on the surface of the substrate film 11. By forming the underlayer, it is possible to enhance surface free energy of the substrate film 11, application properties of various materials (a photocurable resin used as a material of the micro concavo-convex structure 12, for example), a surface slip property, flatness, and the like. A material forming the underlayer is not particularly limited as long as the material can achieve the above object. Examples of the material forming the underlayer include an organo alkoxy metal compound, polyester, acrylic-modified polyester, and polyurethane. Corona discharge processing, UV irradiation processing, or the like may be performed on the surface of the substrate film 11 instead of forming the underlayer.

When the eyeglasses 4 are used to view a 3D image based on a circular polarization scheme, the eyeglasses protection device 1 is required to suppress disturbance of polarization. Disturbance of the polarization of the 3D image due to the eyeglasses protection device 1 may cause problems such as crosstalk. Here, the crosstalk means that the right eye image is seen by the left eye and the left eye image is seen by the right eye. In order to improve visibility of the 3D image, it is preferable that crosstalk occur as little as possible. A crosstalk value is known as a scale of crosstalk, and a range of the crosstalk value allowable for the 3D image is from 5% to 10% in some cases.

As a method of setting the crosstalk value within the above range, a method of setting an in-plane retardation value of the eyeglasses protection device 1 to be equal to or less than 100 nm with respect to a wavelength of visible light is exemplified. As one method of setting the in-plane retardation value of the eyeglasses protection device 1 to a value within the above range, a method of forming the substrate film 11 of a non-stretched film is exemplified. Since the non-stretched film has a lower molecular orientation property than a stretched film and has small deviation in orientation, it is possible to set a small in-plane retardation value and thereby to set a small crosstalk value.

Therefore, when the eyeglasses 4 are used for viewing the 3D image based on the circular polarization scheme, the substrate film 11 is preferably formed of the non-stretched film. In such a case, it is possible to set the in-plane retardation value of the eyeglasses protection device 1 to be equal to or less than 100 nm with respect to the wavelength of visible light. Examples of the material forming the non-stretched film include polycarbonate, polyethylene terephthalate, triacetyl cellulose, polyester, polyethylene naphthalate, polystyrene, polyurethane, polyvinyl alcohol, polymethyl methacrylate, cycloolefin, polypropylene, and polyethylene from among the materials exemplified above. Polycarbonate is preferably used in view of shock resistance and versatility.

The in-plane retardation value of the eyeglasses protection device 1 is preferably equal to or less than 100 nm, is more preferably equal to or less than 30 nm, and is more preferably equal to or less than 20 nm. By setting the in-plane retardation value of the eyeglasses protection device 1 to a value within these ranges, it is possible to further suppress crosstalk. The in-plane retardation value of the eyeglasses protection device 1 can be adjusted by selecting the material of the non-stretching film exemplified above and the thickness of the substrate film 11, for example. Also, the retardation value can be measured by various phase difference measurement devices.

The thickness of the substrate film 11 is not particularly limited and may be appropriately selected in accordance with a purpose of use of the eyeglasses protection device 1. The thickness of the substrate film 11 may be from about 10 μm to about 500 μm, for example. The "film" in the embodiment includes a "sheet," a "plate," and the like.

(2-2. Configuration of Micro Concavo-Convex Structure)

Figure 4:
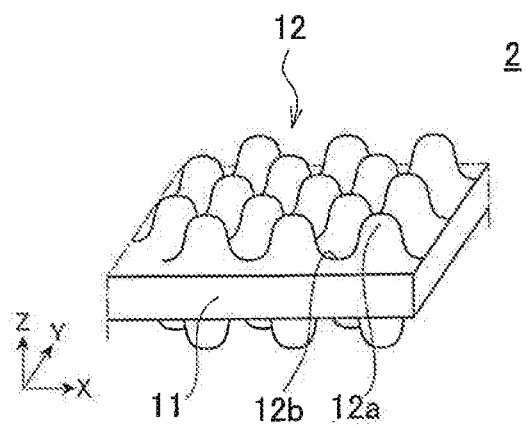
FIG. 4 is a perspective view illustrating an example of the lens surface protective part.

Next, a configuration of the micro concavo-convex structure 12 will be described. The micro concavo-convex structure 12 includes a plurality of convex parts 12a that protrude in a film thickness direction of the substrate film 11 and a plurality of concave portions 12b that are recessed in the film thickness direction of the substrate film 11. The convex parts 12a and the concave parts 12b are periodically arranged on the substrate film 11. In the example of FIG. 4, the convex parts 12a and the concave parts 12b are arranged in a houndstooth pattern. It is a matter of course that the convex parts 12a and the concave parts 12b may be arranged in another arrangement pattern. For example, the convex parts 12a and the concave parts 12b may be arranged in a rectangular check pattern. Alternatively, the convex parts 12a and the concave parts 12b may be randomly arranged. Shapes of the convex parts 12a and the concave parts 12b are not particularly limited. The shapes of the convex parts 12a and the concave parts 12b may be a conical shape, a columnar shape, or a needle shape, for example. The shape of the concave parts 12b is a shape formed by inner wall surfaces of the concave parts 12b.

An average period of the concavo-convex parts of the micro concavo-convex structure 12 is equal to or less than the wavelength of visible light (for example, equal to or less than 830 nm), is preferably equal to or greater than 100 nm and equal to or less than 350 nm, and is further preferably equal to or greater than 150 nm and equal to or less than 280 nm. Therefore, the micro concavo-convex structure 12 is a so-called moth-eye structure. Here, an average period of less than 100 nm is not preferable because there is a possibility of the micro concavo-convex structure 12 becoming difficult to form. Also, an average period of greater than 350 nm is not preferable because there is a possibility of a diffraction phenomenon of visible light occurring.

The average period of the micro concavo-convex structure 12 is an arithmetic mean value of distances between mutually adjacent convex parts 12a and concave parts 12b. The micro concavo-convex structure 12 can be observed with a scanning electron microscope (SEM) or a cross-sectional transmission electron microscope (cross-sectional TEM), for example. A method of calculating the average period is as follows, for example. That is, a plurality of combinations of adjacent concave parts 12b and a plurality of combinations of adjacent convex parts 12a are picked up, and distances thereof are measured. The average period may be calculated by obtaining an arithmetic mean of the measured values. Although the micro concavo-convex structure 12 is formed on both surfaces of the substrate film 11 in FIGS. 3 and 4, the micro concavo-convex structure 12 may be formed on at least one surface.

The micro concavo-convex structure 12 is formed of a hardened curable resin. The hardened curable resin is required to have at least transparency. For example, the refractive index of the hardened curable resin is preferably similar to that of the substrate film 11. It is possible to suppress internal reflection of the lens surface protective part 2 in such a case and to thereby improve contrast of an image viewed through the eyeglasses protection device 1.

The curable resin contains a polymerizable compound and a curing initiator. The polymerizable compound is a resin polymerized and cured by the curing initiator. Examples of the polymerizable compound include an epoxy polymerizable compound and an acrylic polymerizable compound. The epoxy polymerizable compound is a monomer, oligomer, or prepolymer containing one epoxy group or two or more epoxy groups in a molecule. Examples of the epoxy polymerizable compound include various kinds of bisphenol-type epoxy resins (bisphenol A type, F type, and the like), novolac-type epoxy resins, various kinds of modified epoxy resins such as rubber and urethane, a naphthalene-type epoxy resin, a biphenyl-type epoxy resin, a phenol novolac-type epoxy resin, a stilbene-type epoxy resin, a triphenolmethane-type epoxy resin, a dicyclopentadiene-type epoxy resin, a triphenylmethane-type epoxy resin, and a prepolymer thereof.

The acrylic polymerizable compound is a monomer, an oligomer, or a prepolymer containing one acryl group or two or more acryl groups in a molecule. Here, monomers are further classified into monofunctional monomers containing one acryl group in the molecule, bifunctional monomers containing two acryl groups in the molecule, and polyfunctional monomers containing three or more acryl groups in the molecule.

Examples of "monofunctional monomer" include carboxylic acids (acrylic acid), hydroxy compounds (2-hydroxyethyl acrylate, 2-hydroxypropyl acrylate, and 4-hydroxybutyl acrylate), alkyl or alicyclic monomers (isobutyl acrylate, t-butyl acrylate, isooctyl acrylate, lauryl acrylate, stearyl acrylate, isobornyl acrylate, and cyclohexyl acrylate), other functional monomers (2-methoxyethyl acrylate, methoxyethylene glycol acrylate, 2-ethoxyethyl acrylate, tetrahydrofurfuryl acrylate, benzyl acrylate, ethyl carbitol acrylate, phenoxyethyl acrylate, N,N-dimethylaminoethyl acrylate, N,N-dimethylaminopropylacrylamide, N,N-dimethylacrylamide, acryloylmorpholine, N-isopropylacrylamide, N,N-diethylacrylamide, N-vinylpyrrolidone, 2-(perfluorooctyl) ethyl acrylate, 3-perfluorohexyl-2-hydroxypropyl acrylate, 3-perfluorooctyl-2-hydroxypropyl-acrylate, 2-(perfluorodecyl) ethyl-acrylate, 2-(perfluoro-3-methylbutyl) ethyl acrylate), 2,4,6-tribromophenol acrylate, 2,4,6-tribromophenol methacrylate, 2-(2,4,6-tribromophenoxy) ethyl acrylate), and 2-ethylhexyl acrylate.

Examples of "bifunctional monomers" include tri(propylene glycol) diacrylate, trimethylolpropane-diallyl ether, and urethane acrylate.

Examples of "polyfunctional monomers" include trimethylolpropane triacrylate, dipentaerythritol penta-/hexa-acrylate, and ditrimethylolpropane tetraacrylate.

Examples other than the acrylic polymerizable compounds described above include acryl morpholine, glycerol acrylate, polyether-based acrylate, N-vinylformamide, N-vinylcaprolactone, ethoxy diethyleneglycol acrylate, methoxy triethyleneglycol acrylate, polyethyleneglycol acrylate, EO-modified trimethylolpropane triacrylate, EO-modified bisphenol A diacrylate, aliphatic urethane oligomer, and polyester oligomer.

From among the acrylic polymerizable compounds described above, in particular, 2-hydroxyethyl acrylate, acryl morpholine, glycerol acrylate, polyether-based acrylate, N-vinylformamide, N-vinylpyrrolidone, N-vinylcaprolactone, ethoxy diethyleneglycolacrylate, methoxy triethyleneglycolacrylate, polyethyleneglycolacrylate, EO-modified trimethylolpropane triacrylate, EO-modified bisphenol A diacrylate, aliphatic urethane oligomer, polyester oligomer, and the like are preferably used.

The curing initiator is a material for curing the curable resin. Examples of the curing initiator include a thermosetting initiator and a photocuring initiator. The curing initiator may cure the curable resin using an energy beam (an electron beam, for example) other than heat and light. When the curing initiator is a thermosetting initiator, the curable resin is a thermosetting resin. When the curing initiator is a photocuring initiator, the curable resin is a photocurable resin.

Here, the curing initiator is preferably an ultraviolet curing initiator. Therefore, the curable resin is preferably an ultraviolet curable resin. The ultraviolet curing initiator is a kind of photocuring initiator. Examples of the ultraviolet curing initiator include 2,2-dimethoxy-1,2-diphenylethane-1-one, 1-hydroxy-cyclohexylphenylketone, and 2-hydroxy-2-methyl-1-phenylpropane-1-one.

Various additive agents may be added to the curable resin in accordance with a purpose of use of the eyeglasses protection device 1. Examples of such additive agents include an inorganic filler, an organic filler, a leveling agent, a surface conditioner, and an antifoam agent. As types of the inorganic filler, it is possible to exemplify metal oxide fine particles such as $SiO_2$, $TiO_2$, $ZrO_2$, $SnO_2$, and $Al_2O_3$.

The micro concavo-convex structure 12 may be given various properties (hydrophilicity or water repellency, for example) in accordance with a purpose of use of the eyeglasses protection device 1. For example, giving the micro concavo-convex structure 12 hydrophilicity or water repellency in accordance with a purpose of use of the eyeglasses protection device 1 can make the eyeglasses protection device 1 less likely to mist over. In the embodiment, the micro concavo-convex structure 12 preferably has hydrophilicity. As a method of giving the hardened material that forms the micro concavo-convex structure 12 hydrophilicity, it is possible to exemplify a method of using a compound with a hydrophilic functional group (a hydroxyl group, a carboxyl group, a carbonyl group, or the like) as the aforementioned polymerizable compound.

In FIGS. 3 and 4, the micro concavo-convex structure 12 is formed on both surfaces of the substrate film 11. Materials and properties of the micro concavo-convex structure 12 may be the same as or different from each other. That is, the materials and the properties of the micro concavo-convex structure 12 may be determined in accordance with a purpose of use of the eyeglasses protection device 1.

Since the lens surface protective part 2 according to the embodiment is equipped with the micro concavo-convex structure 12 as described above, it is possible to give the lens surface protective part 2 an excellent reflection preventing function. Specifically, the refractive index on a light advancing direction successively varies when light enters the surface of the lens surface protective part 2. When the refractive index steeply varies at any part in the light advancing direction, the part becomes an optical interface. Then, the light is reflected at that part. Since the micro concavo-convex structure 12 is formed on the surface of the lens surface protective part 2 in the embodiment, the refractive index successively varies at that part. That is, the surface of the lens surface protective part 2 is less likely to become the optical interface. Therefore, the lens surface protective part 2 is less likely to reflect light. The refractive index on the light advancing direction successively varies regardless of an incident angle of the light entering the lens surface protective part 2. Therefore, the micro concavo-convex structure 12 can set normal reflectance of the lens surface protective part 2 to be equal to or less than 5%, preferably equal to or less than 1%, and further preferably 0.5% regardless of a reflection angle. The value of the normal reflectance can be adjusted by adjusting the average period or the like of the micro concavo-convex structure 12. In addition, the normal reflectance can be greatly reduced by forming the micro concavo-convex structure 12 on both surfaces of the substrate film 11.

Even when the eyeglasses protection device 1 is used under a light source with significantly high illuminance (equal to or greater than 100,000 lux, for example) such as a shadowless lamp, it is possible to suppress occurrence of reflected light that may enter the eyes of the user of the eyeglasses protection device 1 and thereby to reduce glare and eyestrain due to the reflected light. That is, the eyeglasses protection device 1 can preferably be used as an eyeglasses protection device for medical use.

Figure 5:
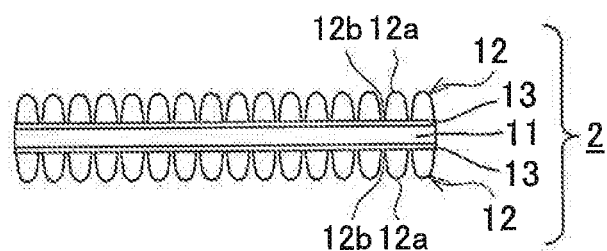
FIG. 5 is a sectional view illustrating a modification example of the lens surface protective part.

Here, the micro concavo-convex structure 12 may be integrally formed with the substrate film 11. In such a case, the substrate film 11 is formed of a material that forms the micro concavo-convex structure 12, namely the curable resin. As illustrated in FIG. 5, a base layer 13 may be formed between the substrate film 11 and the micro concavo-convex structure 12. The base layer 13 is formed of the same material as the micro concavo-convex structure 12, for example. By forming the base layer 13 between the substrate film 11 and the micro concavo-convex structure 12, adhesiveness between the substrate film 11 and the micro concavo-convex structure 12 can be enhanced. The micro concavo-convex structure 12 may be formed on the base layer 13 after the base layer 13 is formed on the substrate film 11, or the micro concavo-convex structure 12 and the base layer 13 may be integrally formed on the substrate film 11.

<3. Configuration of Temple Protective Parts>

Figure 6:
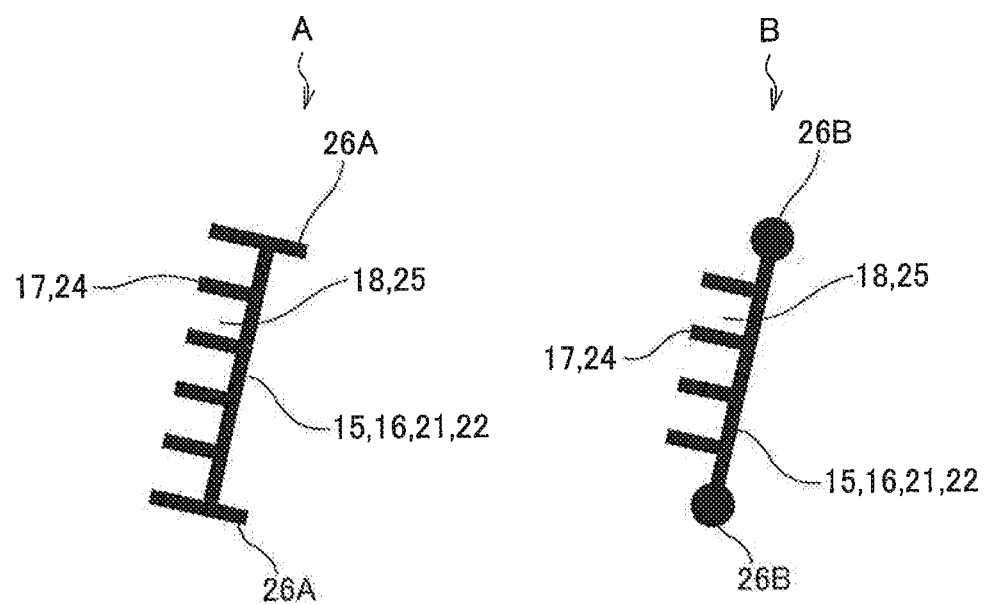
FIG. 6 is an explanatory diagram illustrating an example of an insertion hole and a circumferential structure thereof.

Next, a configuration of the temple protective parts 3 will be described based on FIGS. 1, 2, and 6. As described above, the temple protective parts 3 are provided at both ends of the lens surface protective part 2 in the length direction and protect the temples 5 of the eyeglasses 4. That is, the temple protective parts 3 are arranged outside the temples 5 when the eyeglasses protection device 1 is attached to the eyeglasses 4. The length of the temple protective parts 3 in the vertical direction is preferably longer than the length of the temples 5 in the vertical direction. In the embodiment, the eyeglasses protection device 1 is manufactured by cutting a reflection protective film 110 equipped with the substrate film 11 and the micro concavo-convex structure 12 into the shape of the eyeglasses protection device 1 as will be described later in detail. Therefore, the temple protective parts 3 also include the substrate film 11 and the micro concavo-convex structure 12. However, since the temple protective parts 3 are not necessarily required to have the reflection preventing function, the temple protective parts 3 may be formed of a film different from that of the lens surface protective part 2. In such a case, the eyeglasses protection device 1 may be manufactured by separately manufacturing the temple protective parts 3 and the lens surface protective part 2 and bonding the parts. The temple protective parts 3 are divided into a left temple protective part 31 for protecting the temple 5 on the left side and a right temple protective part 32 for protecting the temple 5 on the right side. The left temple protective part 31 includes an attachment part 3A, and the right temple protective part 32 includes an attachment part 3B. Both of the attachment parts 3A and 3B are for attaching the eyeglasses protection device 1 to the eyeglasses 4 or detaching the eyeglasses protection device 1 from the eyeglasses 4.

(3-1. Configuration of Attachment Part 3A)

Next, a configuration of the attachment part 3A will be described based on FIGS. 1 and 2. The attachment part 3A includes insertion holes 15 and 16, auxiliary cut holes 17, and auxiliary holding parts 18.

The insertion holes 15 and 16 are holes into which the temple 5 is inserted. The insertion holes 15 and 16 extend in a direction substantially perpendicular to an insertion direction of the temple 5. The length of the insertion holes 15 and 16 in the vertical direction is equal to or greater than the length (height) of the temple 5 in the vertical direction. The insertion holes 15 and 16 extend substantially parallel to each other and are aligned in the insertion direction of the temple 5. The insertion holes 15 and 16 are manufactured by forming cut holes at the left temple protective part 31. Additional insertion holes with the same function as the insertion holes 15 and 16 may be formed. That is, the number of the insertion holes may be three or more.

The auxiliary cut holes 17 are cut holes extending from outer edges of the insertion holes 15 and 16 toward the outside. Although a plurality of auxiliary cut holes are preferably formed for each of the insertion holes 15 and 16, it is only necessary that one or more auxiliary cut holes be formed for each of the insertion holes 15 and 16. When the temple 5 can be sufficiently held only by the insertion holes 15 and 16, the auxiliary cut holes 17 may be omitted.

Although the auxiliary cut holes 17 preferably extend in a perpendicular direction from the insertion holes 15 and 16 as illustrated in FIG. 1, the auxiliary cut holes 17 may extend in an oblique direction from the insertion holes 15 and 16.

The auxiliary holding parts 18 are parts formed in the circumferences of the insertion holes 15 and 16 by the auxiliary cut holes 17 and hold the temple 5 when the temple 5 is inserted into the insertion holes 15 and 16.

The attachment part 3A holds the temple 5 as follows. That is, the user arranges the eyeglasses 4 on the rear surface side of the eyeglasses protection device 1 and inserts the temple 5 into the insertion holes 15 and 16 in order. The insertion holes 15 and 16 hold the temple 5. Furthermore, the temple 5 is pinched between a portion arranged between the insertion holes 15 and 16 and portions arranged outside the insertion holes 15 and 16 from among the portions forming the left temple protective part 31. That is, these portions pinch the temple 5 by elastic restoring force. Furthermore, the auxiliary holding parts 18 also hold the temple 5.

As described above, the attachment part 3A holds the temple 5 with the insertion holes 15 and 16, the portion arranged between the insertion holes 15 and 16, the portions arranged outside the insertion holes 15 and 16, and the auxiliary holding parts 18. Since the temple 5 can be further firmly held by the auxiliary holding parts 18, it is possible to suppress positional deviation of the temple 5, rattling, and the like even when the length of the insertion holes 15 and 16 in the vertical direction is greater than the length of the temple 5 in the vertical direction. Also, the user can move the temple 5 in the insertion direction. In this way, the user can adjust the attachment position of the eyeglasses protection device 1.

(3-2. Configuration of Attachment Part 3B)

Next, a configuration of the attachment part 3B will be described based on FIGS. 1 and 2. The attachment part 3B includes insertion holes 21 and 22, a traverse cut hole 23, an upper holding part 20A, a lower holding part 20B, auxiliary cut holes 24, and auxiliary holding parts 25.

The insertion holes 21 and 22, the auxiliary cut holes 24, and the auxiliary holding parts 25 are the same as the insertion holes 15 and 16, the auxiliary cut holes 17, and the auxiliary holding parts 18.

The traverse cut hole 23 is a cut hole crossing between the adjacent insertion holes 21 and 22 in an oblique direction. The upper holding part 20A and the lower holding part 20B are parts formed by the insertion holes 21 and 22 and the traverse cut hole 23. That is, the portion arranged between the insertion holes 21 and 22 from among the portions forming the right temple protective part 32 is divided into the upper holding part 20A and the lower holding part 20B by the traverse cut hole 23.

The attachment part 3B holds the temple 5 as follows. The user fixes the left temple protective part 31 to the temple 5. Then, the user causes the attachment part 3A to approach the side of the lens surface 4a of the eyeglasses 4. Then, the user covers the lens surface 4a with the lens surface protective part 2 and arranges the right temple protective part 32 outside the temple 5. Then, the user arranges the upper holding part 20A and the lower holding part 20B inside the temple 5 by pressing the upper holding part 20A and the lower holding part 20B thereinto from the outside.

In this way, the insertion holes 21 and 22 hold the temple 5. Furthermore, the temple 5 is pinched by the upper holding part 20A, the lower holding part 20B, and portions arranged outside the insertion holes 21 and 22. That is, these portions pinch the temple 5 by elastic restoring force. Furthermore, the auxiliary holding parts 25 also hold the temple 5.

As described above, the attachment part 3B holds the temple 5 with the insertion holes 21 and 22, the upper holding part 20A, the lower holding part 20B, the portions arranged outside the insertion holes 21 and 22, and the auxiliary holding parts 25. Since the auxiliary holding parts 25 can further firmly hold the temple 5, it is possible to suppress positional deviation of the temple 5, rattling, and the like even when the length of the insertion holes 21 and 22 in the vertical direction is greater than the length of the temple 5 in the vertical direction. Also, the user can move the temple 5 in the insertion direction. In this way, the user can adjust the attachment position of the eyeglasses protection device 1.

Furthermore, the traverse cut hole 23 is formed between the upper holding part 20A and the lower holding part 20B. Therefore, it is only necessary for the user to detach the temple 5 from the right temple protective part 32 while pressing the upper holding part 20A and the lower holding part 20B in the vertical direction for detaching the right temple protective part 32 from the temple 5. As described above, the user can easily detach the right temple protective part 32 from the temple 5.

Furthermore, the attachment part 3A is formed at the left temple protective part 31, and the attachment part 3B is formed at the right temple protective part 32. In other words, the traverse cut hole 23 is formed only at the attachment part 3B. Therefore, the eyeglasses protection device 1 is configured such that the temple 5 can be easily detached from the attachment part 3B while the temple protective parts 3 are firmly held at the temples 5 by the attachment parts 3A and 3B. Therefore, it is possible to firmly hold the temple 5 with the attachment part 3A even if the temple 5 falls from the attachment part 3B. That is, the eyeglasses protection device 1 is less likely to fall from the eyeglasses 4. The installation positions of the attachment parts 3A and 3B may be opposite in the horizontal direction. Furthermore, the attachment part 3A may be formed at both the left temple protective part 31 and the right temple protective part 32, or the attachment part 3B may be formed at both the left temple protective part 31 and the right temple protective part 32. However, the attachment part 3A is preferably formed at one of the temple protective parts 3 while the attachment part 3B is formed at the other in order to achieve both firm holding and easy detachment.

When holding force of the attachment parts 3A and 3B is not sufficient, the attachment part 3B and the temple 5 may be attached to each other with an adhesive tape, for example. Also, the attachment parts 3A and 3B may be omitted, and in such a case, the temple protective parts 3 may be fixed to the temples 5 with an adhesive tape or the like.

(3-3. Configuration of Breakage Suppression Hole)

As illustrated in FIGS. 6(A) and 6(B), breakage suppression holes 26A and 26B may be formed at upper and lower ends of the insertion holes 15, 16, 21, and 22. The breakage suppression hole 26A is a cut hole extending in a direction perpendicular to a length direction of the insertion holes 15, 16, 21, and 22. It is only necessary for the breakage suppression hole 26A to extend in a direction intersecting the length direction of the insertion holes 15, 16, 21, and 22. The breakage suppression hole 26B is a hole with a diameter that is greater than the width of the insertion holes 15, 16, 21, and 22. By forming the breakage suppression holes 26A and 26B at the upper and lower ends of the insertion holes 15, 16, 21, and 22, it is possible to suppress breakage of the temple protective parts 3 when a large burden is imparted on the upper and lower ends of the insertion holes 15, 16, 21, and 22 when the temples 5 are attached or detached, for example.

(3-4. Configuration of Cut Grooves)

Figure 7:
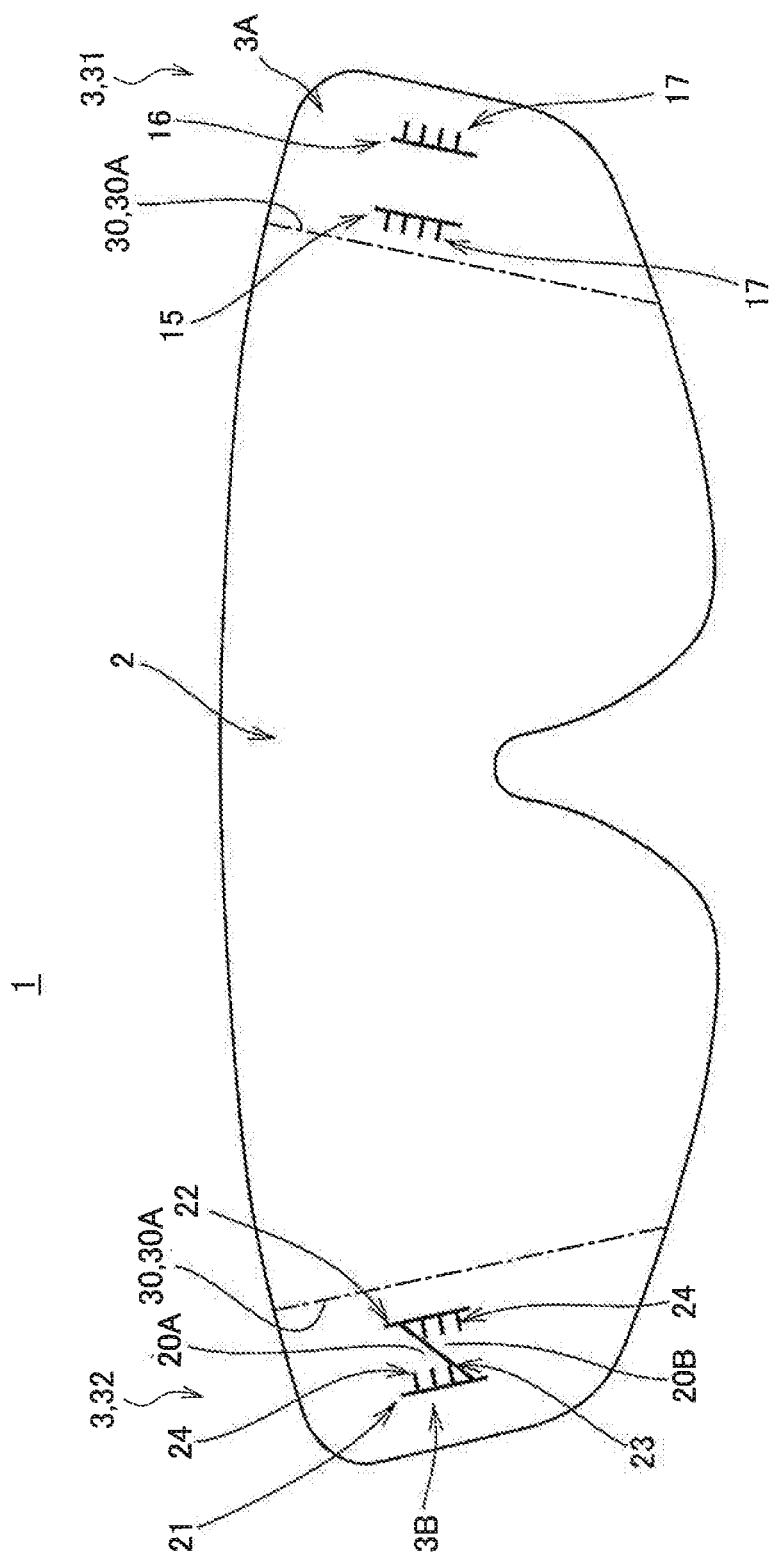
FIG. 7 is a front view illustrating a state in which a cut groove is provided at a boundary line between the lens surface protective part and a temple protective part.

As illustrated in FIG. 7, first cut grooves 30A may be formed at boundary lines 30 between the lens surface protective part 2 and the temple protective parts 3. The first cut grooves 30A are formed on the surface (the surface on the side opposite to the surface that faces the user) of the eyeglasses protection device 1. The first cut grooves 30A do not penetrate the eyeglasses protection device 1. That is, the depth of the first cut grooves 30A is smaller than the thickness of the eyeglasses protection device 1. For example, the depth of the first cut grooves 30A is about a half of the thickness of the eyeglasses protection device 1. By forming the first cut grooves 30A at the boundary lines 30 between the lens surface protective part 2 and the temple protective parts 3, it becomes easier to deform the eyeglasses protection device 1 along the shape of the eyeglasses 4. When the first cut groove 30A is not between the right temple protective part 32 and the lens surface protective part 2, for example, there is a possibility of the right temple protective part 32 falling off of the temple 5 due to elastic restoring force thereof. However, forming the first cut groove 30A between the right temple protective part 32 and the lens surface protective part 2 makes it possible to cause the right temple protective part 32 to be less likely to fall off of the temple 5.

Figure 8:
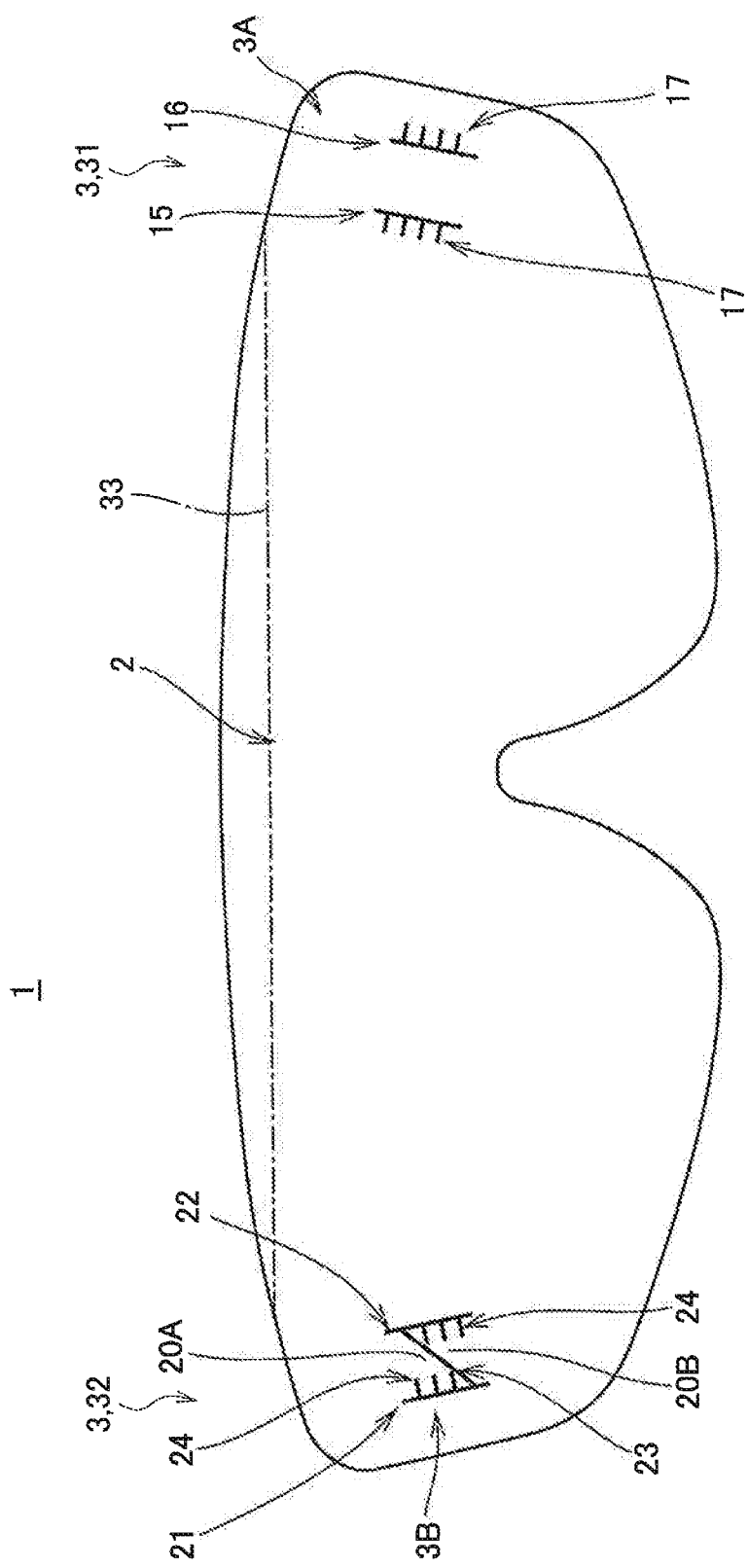
FIG. 8 is a front view illustrating a state in which the cut groove is provided at an upper end of the lens surface protective part.

As illustrated in FIG. 8, a second cut groove 33 may be formed to cross the lens surface protective part 2 on the side of the upper end thereof. The second cut groove 33 is formed on the surface (the surface on the side opposite to the surface that faces the user) of the eyeglasses protection device 1. The second cut groove 33 does not penetrate the eyeglasses protection device 1. That is, the depth of the cut groove 33 is smaller than the thickness of the eyeglasses protection device 1. For example, the depth of the cut groove 33 is about a half of the thickness of the eyeglasses protection device 1. Forming the second cut groove 33 crossing the lens surface protective part 2 on the side of the upper end thereof makes it possible for the user to easily fold the lens surface protective part 2 on the side of the upper end thereof toward the inner side (the side of the user). In such a case, the eyeglasses protection device 1 can more reliably protect the user from airborne substances.

<4. Method of Using Eyeglasses Protection Device>

Next, a method of using the eyeglasses protection device 1 will be described. The user attaches the eyeglasses protection device 1 to the eyeglasses 4 using the following method. First, the user arranges the eyeglasses 4 on the rear surface side of the eyeglasses protection device 1 and inserts the temple 5 into the insertion holes 15 and 16 in order. In this way, the user causes the left temple protective part 31 to be held by the temple 5. Then, the user causes the attachment part 3A to approach the side of the lens surface 4a of the eyeglasses 4. Then, the user covers the lens surface 4a with the lens surface protective part 2 and arranges the right temple protective part 32 outside the temple 5. Then, the user arranges the upper holding part 20A and the lower holding part 20B inside by pressing the upper holding part 20A and the lower holding part 20B thereinto from the outside. In this way, the user causes the right temple protective part 32 to be held by the temple 5. The user attaches the eyeglasses protection device 1 to the eyeglasses 4 through the above processes. Thereafter, the user wears the eyeglasses 4 to which the eyeglasses protection device 1 has been attached and performs various operations.

The user detaches the eyeglasses protection device 1 from the eyeglasses 4 using the following method. First, the user detaches the temple 5 from the right temple protective part 32 while pressing the upper holding part 20A and the lower holding part 20B in the vertical direction. Then, the user pulls temple 5 out of the insertion holes 15 and 16. In this way, the user detaches the left temple protective part 31 from the temple 5. The user detaches the eyeglasses protection device 1 from the eyeglasses 4 through the above processes.

As described above, the eyeglasses protection device 1 can protect the user from various airborne substances by being attached to the eyeglasses. Furthermore, the lens surface protective part 2 is formed of a material with transparency, and the in-plane retardation value is equal to or less than 100 nm with respect to the wavelength of visible light. Therefore, the eyeglasses protection device 1 can maintain visibility and operability for the user even when the user views a 3D image.

Furthermore, since the micro concavo-convex structure 12 is formed on the surface of the lens surface protective part 2, it is possible to suppress occurrence of reflected light that may enter the eyes of the user of the eyeglasses protection device 1. Therefore, it is possible to suppress glare and eyestrain of the user due to the reflected light. Also, the micro concavo-convex structure 12 can suppress occurrence of reflected light in a wider wavelength band than a reflection protective film that is used in a liquid crystal display or the like and responds to a specific wavelength. Therefore, the user can view an operation target with substantially the same color both in a case in which the user views the operation target through the lens surface protective part 2 and in a case in which the user views the operation target without the lens surface protective part 2. Also, the user who wears the eyeglasses protection device 1 can easily cope with variations in illuminance even if circumferential illuminance greatly varies. The eyeglasses protection device 1 can be used not only for medical use but for various purposes of use.

Figure 9:
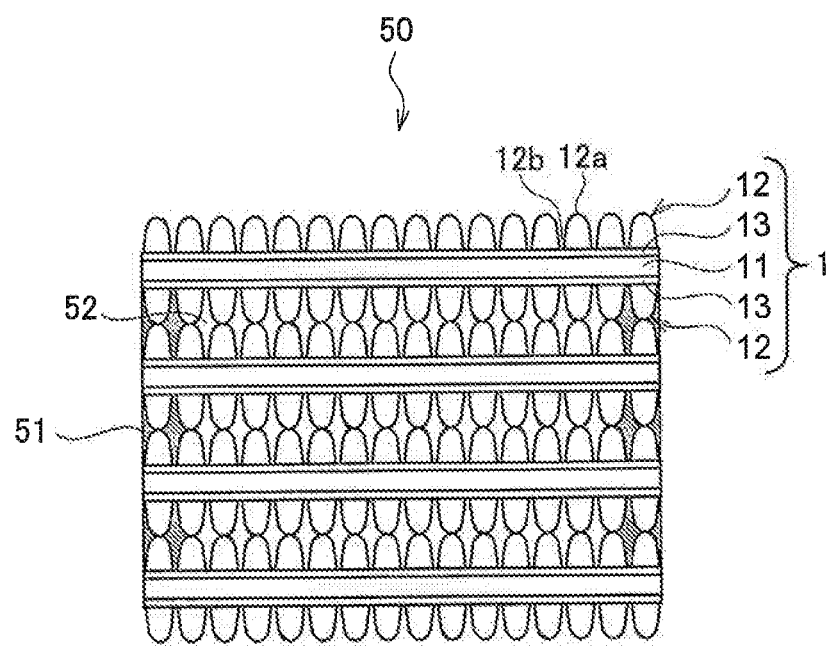
FIG. 9 is a side sectional view illustrating an eyeglasses protection device laminated article.

As illustrated in FIG. 9, an eyeglasses protection device laminated article 50 may be formed by laminating a plurality of eyeglasses protection devices 1. The plurality of eyeglasses protection devices 1 are bonded to each other by adhesive layers 51. The eyeglasses protection devices 1 can be attached and detached. The adhesive layers 51 may be formed only at a part of the interfaces between the plurality of eyeglasses protection devices 1. In such a case, a part of the interfaces forms a space 52. In such a case, the adhesive layers 51 are preferably formed at positions at which the adhesive layers 51 do not obstruct a field of view of the user, such as at an outer circumferential portion of the lens surface protective part 2 or at temple protective parts 3. When the adhesive layers 51 are formed at the temple protective parts 3, the adhesive layers 51 may be formed to have a predetermined length in the vertical direction of the temple protective parts 3, for example. Alternatively, the adhesive layers 51 may be formed at a predetermined interval in the vertical direction of the temple protective parts 3. When the adhesive layers 51 are formed only at a part of the interfaces between the plurality of eyeglasses protection devices 1, a peeling property of the eyeglasses protection devices 1 is enhanced. Also, since the adhesive layers 51 are not likely to remain on the eyeglasses protection device laminated article 50, it is possible to suppress degradation of visibility due to remaining substances (residues) of the adhesive layers 51. In addition, it is possible to suppress variations in the thickness of the eyeglasses protection device laminated article 50 due to the adhesive layers 51.

The plurality of eyeglasses protection devices 1 may or may not be in contact with each other at these interfaces. Tip ends of the convex parts 12*a* of the micro concavo-convex structure 12 may or may not be in contact with each other. Alternatively, the convex parts 12*a* of one eyeglasses protection device 1 may enter the concave parts 12*b* of another eyeglasses protection device 1. When the convex parts 12*a* and the concave parts 12*b* of the micro concavo-convex structure 12 are regularly aligned, satisfactory adhesiveness is obtained at the interfaces between the plurality of eyeglasses protection devices 1.

The following effects can be expected as well as the aforementioned effects when the plurality of eyeglasses protection devices 1 are laminated. The user can peel the frontmost eyeglasses protection device 1 from the eyeglasses protection device laminated article 50 when the eyeglasses protection device 1 is contaminated by airborne substances. In such a case, the user can immediately recover the field of view when the airborne substances obstruct the field of view. Also, it is not necessary for the user to remove (wipe, for example) the airborne substances from the eyeglasses protection device laminated article 50 even when the airborne substances obstruct the field of view. Further, when the airborne substances have an adverse effect on the human body, the user should not touch the airborne substances. In such a case, the user can recover the field of view without touching the airborne substances.

Also, the space 52 at the interfaces formed between the plurality of eyeglasses protection devices 1, if there is any, does not substantially damage transparency. In addition, the micro concavo-convex structure 12 can suppress occurrence of reflected light at the interfaces between the plurality of eyeglasses protection devices 1. When the highest priority is placed on the transparency of the eyeglasses protection device laminated article 50, the adhesive layers 51 may be formed on the entire interfaces between the plurality of eyeglasses protection devices 1. In such a case, a composition of the adhesive layers 51 is selected such that the refractive index of the adhesive layers 51 is a value that does not disturb visibility.

<5. Configuration of Original Board>

Figure 10:
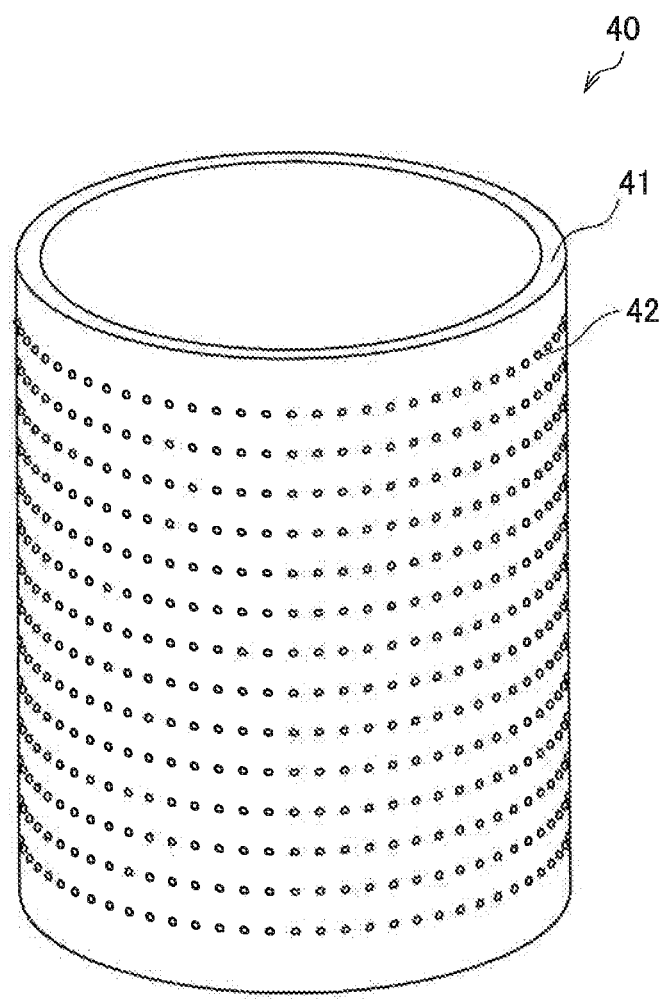
FIG. 10 is a perspective view illustrating an exemplary appearance of an original board with a micro concavo-convex structure formed in a circumferential surface thereof.

The micro concavo-convex structure 12 is manufactured using an original board 40 illustrated in FIG. 10. A configuration of the original board 40 will be described below. The original board 40 is an original board used in a nanoimprint method, for example, and has a cylindrical shape. The original board 40 may have a columnar shape or another shape (a plate shape, for example). However, when the original board 40 has a columnar shape or a cylindrical shape, a micro concavo-convex structure 42 of the original board 40 can be transferred to a resin base material or the like in a seamless manner by a roll-to-roll scheme. In this way, it is possible to manufacture the reflection protective film 110 (see FIG. 13) to which the micro concavo-convex structure 42 of the original board 40 has been transferred at high production efficiency. The reflection protective film 110 is a film equipped with the substrate film 11 and the micro concavo-convex structure 12, and the eyeglasses protection device 1 is manufactured by cutting the reflection protective film 110 into the shape of the eyeglasses protection device 1. From this viewpoint, the shape of the original board 40 is preferably a cylindrical shape or a columnar shape.

The original board 40 is equipped with an original board base material 41 and the micro concavo-convex structure 42 formed on the surface of the original board base material 41. The original board base material 41 is a glass body, for example, and specifically, is made of silica glass. However, the original board base material 41 is not particularly limited as long as SiO$_2$ purity is high, and the original board base material 41 may be formed of fused silica glass, synthesized silica glass, or the like. Although the shape of the original board base material 41 is a cylindrical shape, a columnar shape or another shape is also applicable. However, the original board base material 41 preferably has a cylindrical shape or a columnar shape as described above. The micro concavo-convex structure 42 has an inverted shape compared to the micro concavo-convex structure 12.

<6. Method of Manufacturing Original Board>

Next, a method of manufacturing the original board will be described. First a base material resist layer is formed (film formation) on the original board base material 41. Here, a resist material forming the base material resist layer is not particularly limited, and any of an organic resist material and an inorganic resist material may be used. Examples of the organic resist material include a novolac-based resist or a chemically amplified resist. Examples of the inorganic resist material include a metal oxide containing one kind or two or more kinds of transition metals such as tungsten (W) or molybdenum (Mo). However, the base material resist layer is preferably formed of a thermal-reaction-type resist containing a metal oxide in order to perform thermal reaction lithography.

In the case of using the organic resist material, the base material resist layer may be formed on the original board base material 41 using spin coating, slit coating, dip coating, spray coating, screen printing, or the like. In the case of using the inorganic resist material for the base material resist layer, the base material resist layer may be formed using a sputtering method.

Figure 11:
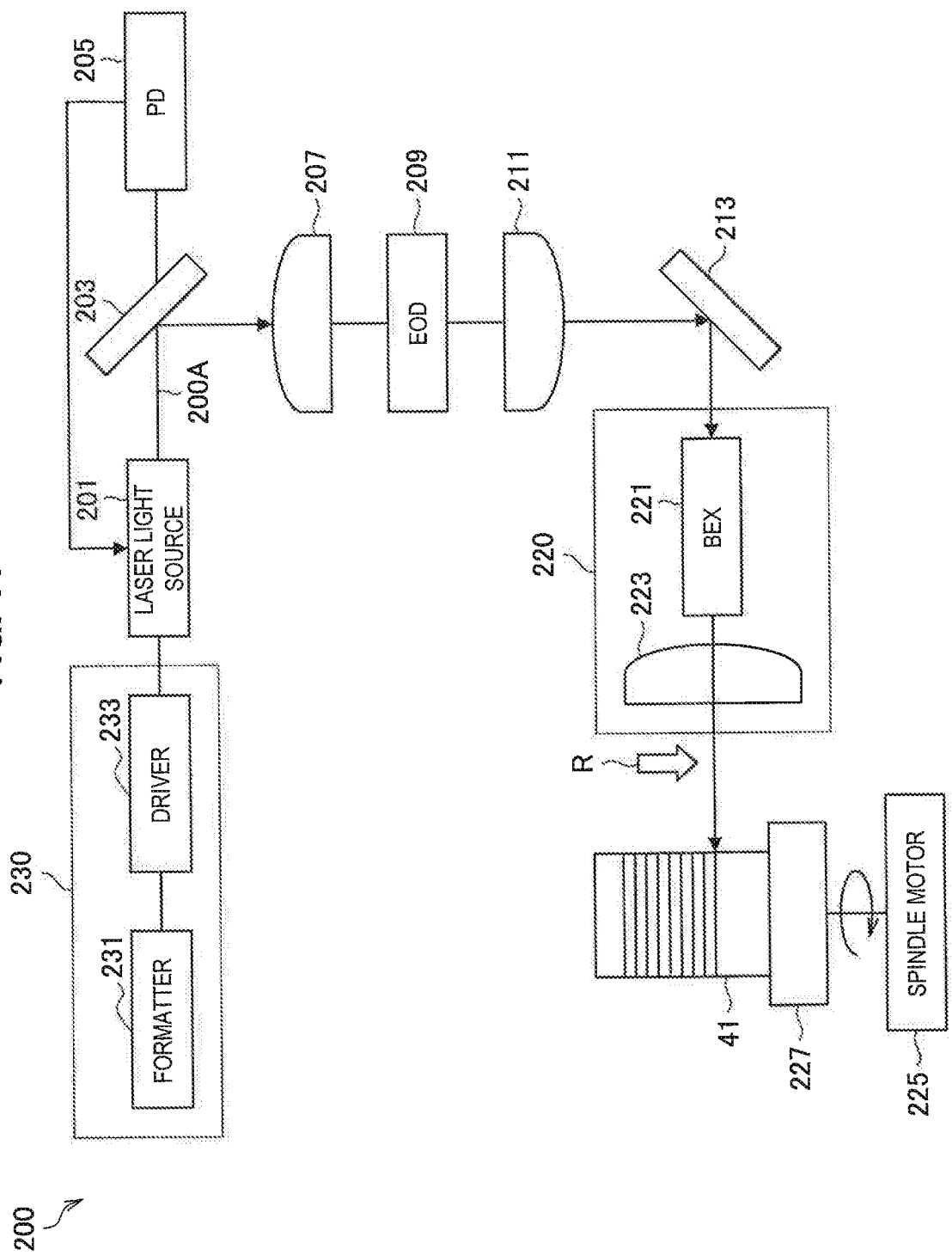
FIG. 11 is a block diagram illustrating a configuration example of an exposure device.

Next, a latent image is formed on the base material resist layer by exposing a part of the base material resist layer with an exposure device 200 (see FIG. 11). Specifically, the exposure device 200 modulates laser light 200A and irradiates the base material resist layer with the laser light 200A. In this way, since the part of the base material resist layer that is irradiated with the laser light 200A is modified, the latent image corresponding to the micro concavo-convex structure 42 can be formed on the base material resist layer. The latent image is formed on the base material resist layer in an average period of equal to or less than the wavelength of visible light.

Subsequently, the base material resist layer is developed by dropping a developer onto the base material resist layer on which the latent image has been formed. In this way, the micro concavo-convex structure is formed on the base material resist layer. Then, the micro concavo-convex structure 42 is formed on the original board base material 41 by etching the original board base material 41 and the base material resist layer by using the base material resist layer as a mask. Although an etching method is not particularly limited, dry etching with perpendicular anisotropy is preferably performed, and for example, Reactive Ion Etching (RIE) is preferably performed. The original board 40 is manufactured through the aforementioned processes.

<7. Configuration of Exposure Device>

Next, a configuration of the exposure device 200 will be described based on FIG. 11. The exposure device 200 is a device for exposing the base material resist layer. The exposure device 200 is equipped with a laser light source 201, a first mirror 203, a photodiode (PD) 205, a polarization optical system, a control mechanism 230, a second mirror 213, a moving optical table 220, a spindle motor 225, and a turn table 227. The original board base material 41 is placed on the turn table 227 and can rotate.

The laser light source 201 is a light source that emits the laser light 200A and is a solid laser or a semiconductor laser, for example. Although a wavelength of the laser light 200A emitted by the laser light source 201 is not particularly limited, the wavelength may be in a blue light band from 400 nm to 500 nm, for example. In addition, the laser light 200A may have any spot diameter (the diameter of a spot with which the resist layer is irradiated) as long as the spot diameter is smaller than the diameter of the opening surfaces of the concave parts of the micro concavo-convex structure 42, and the spot diameter may be about 200 nm, for example. The laser light 200A emitted from the laser light source 201 is controlled by the control mechanism 230.

The laser light 200A emitted from the laser light source 201 advances straight as a parallel beam, is reflected by the first mirror 203, and is guided into the polarization optical system.

The first mirror 203 is formed of a polarization beam splitter and has a function of reflecting one polarization component and transmitting the other polarization component. The polarization component that has penetrated the first mirror 203 is received by the photodiode 205 and is subjected to photoelectric conversion. A received light signal obtained by the photoelectric conversion performed by the photodiode 205 is input to the laser light source 201, and the laser light source 201 performs phase modulation of the laser light 200A based on the input received light signal.

The polarization optical system is equipped with a condenser lens 207, an Electro Optic Deflector (EOD) 209, and a collimator lens 211.

In the polarization optical system, the laser light 200A is collected by the electro optic deflector 209 through the condenser lens 207. The electro optic deflector 209 is an element capable of controlling an irradiation position of the laser light 200A. The exposure device 200 can also change the irradiation position of the laser light 200A guided onto the moving optical table 220 by the electro optic deflector 209. The irradiation position of the laser light 200A is adjusted by the electro optic deflector 209, and the laser light 200A is then formed into a parallel beam again by the collimator lens 211. The laser light 200A emitted from the polarization optical system is reflected by the second mirror 213 and is guided onto the moving optical table 220 in a horizontal and parallel manner.

The moving optical table 220 is equipped with a Beam expander (BEX) 221 and an objective lens 223. The laser light 200A guided to the moving optical table 220 is formed into a desired beam shape by the beam expander 221, and the base material resist layer formed on the original board base material 41 is then irradiated with the laser light 200A via the objective lens 223. The moving optical table 220 moves in a direction of the arrow R (a feed pitch direction) by a single feed pitch (track pitch) every time the original board base material 41 rotates once. The original board base material 41 is installed on the turn table 227. The spindle motor 225 rotates the original board base material 41 by rotating the turn table 227.

The control mechanism 230 is equipped with a formatter 231 and a driver 233 and controls irradiation with the laser light 200A. The formatter 231 generates a modulation signal for controlling irradiation with the laser light 200A, and the driver 233 controls the laser light source 201 based on the modulation signal generated by the formatter 231. In this way, the irradiation of the original board base material 41 with the laser light 200A is controlled.

The formatter 231 generates a control signal for irradiating the base material resist layer with the laser light 200A based on an input image of an arbitrary pattern depicted on the base material resist layer. Specifically, the formatter 231 acquires an input image of an arbitrary pattern to be depicted on the base material resist layer first. The input image is an image corresponding to a developed diagram of an outer circumferential surface of the base material resist layer obtained by cutting the outer circumferential surface of the base material resist layer in an axial direction and expanding the outer circumferential surface in a plane. Next, the formatter 231 divides the input image into small regions with a predetermined size (divides the input image in a lattice shape, for example) and determines whether or not the depicted image pattern is included in each of the small regions. Subsequently, the formatter 231 generates a control signal for performing control to irradiate the small regions that have been determined to include the depicted image pattern with the laser light 200A. Furthermore, the driver 233 controls an output of the laser light source 201 based on the control signal generated by the formatter 231. In this way, the irradiation of the base material resist layer with the laser light 200A is controlled.

<8. Method of Manufacturing Reflection Protective Film Using Original Board>

(8-1. Outline)

Figure 12:
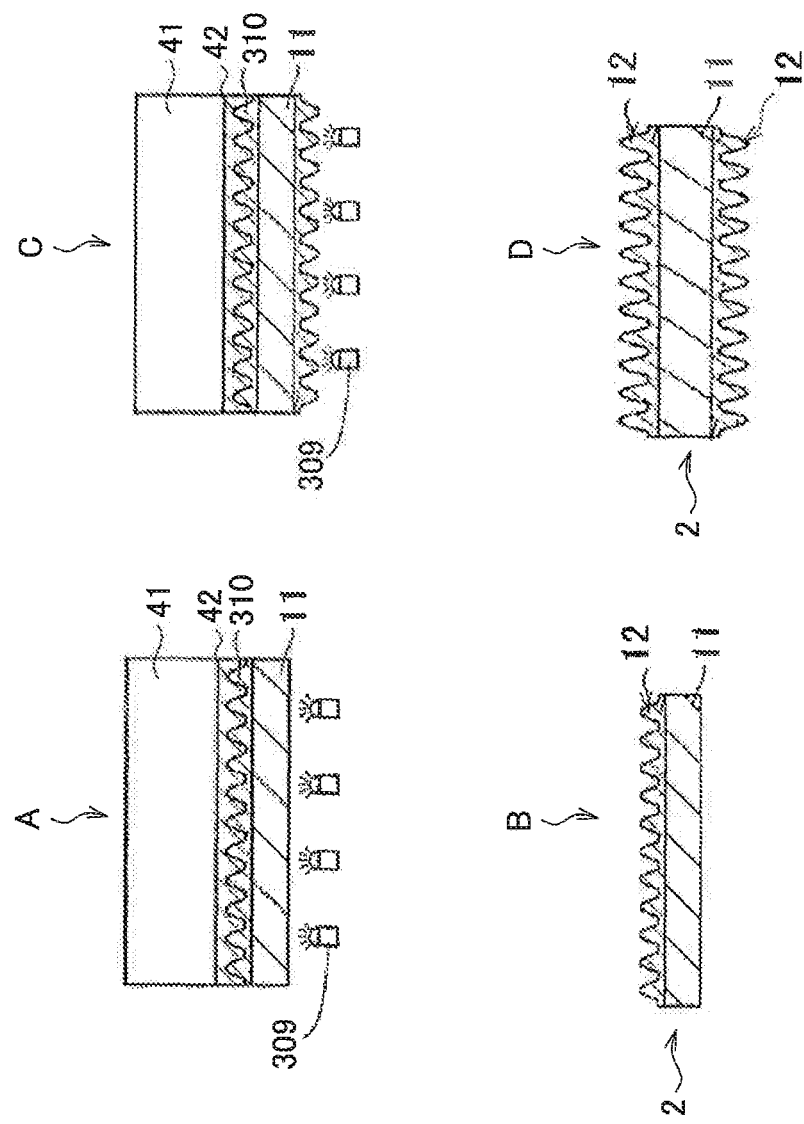
FIG. 12 is a side sectional view illustrating processes of manufacturing a reflection protective film.

First, an outline of a method of manufacturing the reflection protective film 110 using the original board 40 will be described based on FIG. 12. First, an uncured resin layer 310 is formed by applying an uncured curable resin to the substrate film 11 as illustrated in FIG. 12(A). Then, the micro concavo-convex structure 42 of the original board 40 is pressed onto the uncured resin layer 310. Then, the uncured resin layer 310 is cured by irradiating the uncured resin layer 310 with an energy beam from an energy beam source 309. Here, a type of the energy beam emitted from the energy beam source 309 may be selected depending on the type of the curable resin. Examples of the type of the energy beam include an electron beam, an ultraviolet beam, an infrared beam, a laser light beam, a visible light beam, ionizing radiation (such as X rays, α rays, β rays, and γ rays), microwaves, and radio-frequency radiation.

In this way, the micro concavo-convex structure 42 is transferred to the uncured resin layer 310. That is, the micro concavo-convex structure 12 is formed on one surface of the substrate film 11 as illustrated in FIG. 12(B). In this way, a reflection protective film 110 with the micro concavo-convex structure 12 formed on one surface is formed. When it is desired to form the micro concavo-convex structure 12 on both surfaces of the reflection protective film 110, the following process is further performed.

The uncured resin layer 310 is formed by applying an uncured curable resin to the other surface (the surface on which the micro concavo-convex structure 12 is not formed) of the reflection protective film 110 illustrated in FIG. 12(B). Thereafter, the micro concavo-convex structure 42 of the original board 40 is pressed onto the uncured resin layer 310 as illustrated in FIG. 12(C). Then, the uncured resin layer 310 is cured by irradiating the uncured resin layer 310 with an energy beam from the energy beam source 309. In this way, the micro concavo-convex structure 42 is transferred to the uncured resin layer 310. That is, the micro concavo-convex structure 12 is formed on the other surface of the substrate film 11 as illustrated in FIG. 12(D). In this way, the reflection protective film 110 with the micro concavo-convex structure 12 formed on both surfaces is formed. In the aforementioned processes, the base layer 13 may be formed between the micro concavo-convex structure 12 and the substrate film 11. Also, various protective films may be formed on the surface of the reflection protective film 110.

(8-2. Details)

Figure 13:
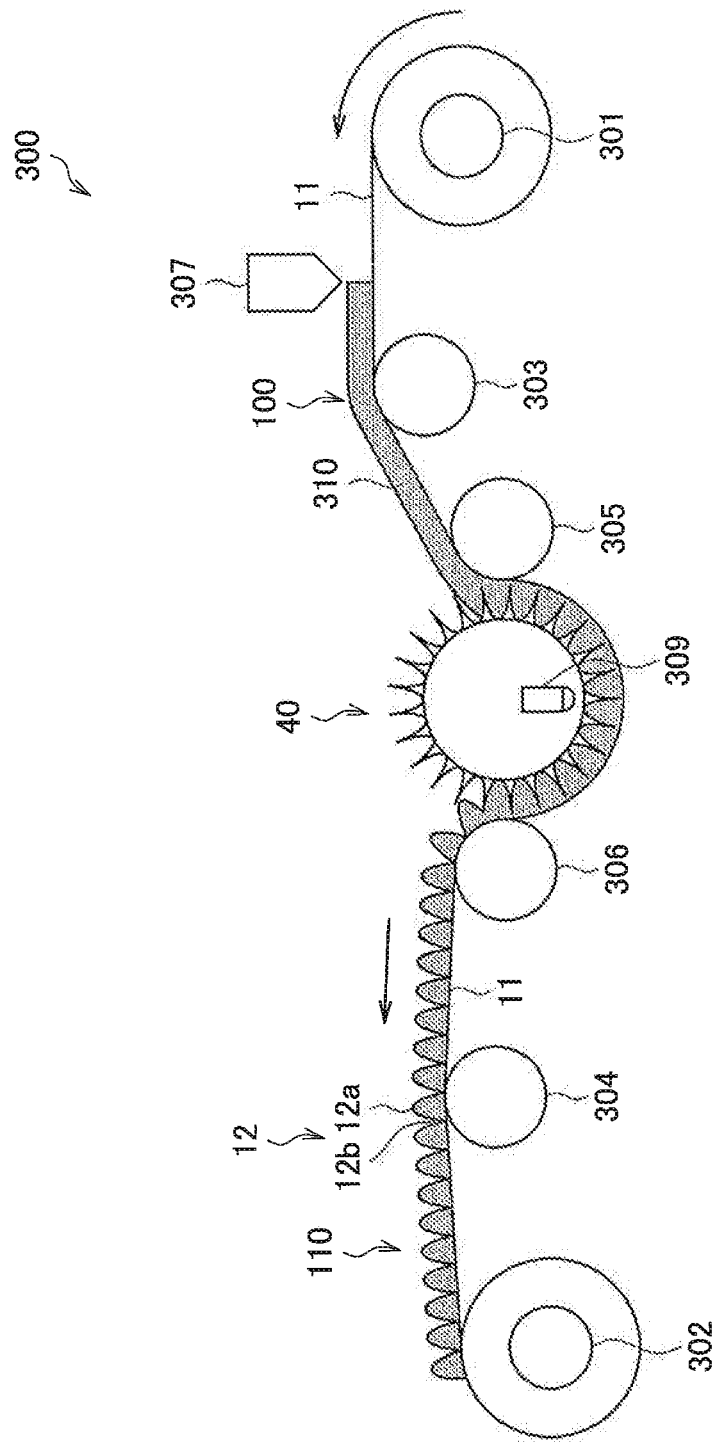
FIG. 13 is a diagram schematically illustrating an example of a transfer device that manufactures the reflection protective film by a roll-to-roll scheme.

Next, a method of manufacturing the reflection protective film 110 using the original board 40 will be described in detail with reference to FIG. 13. A transfer device 300 illustrated in FIG. 13 is a transfer device based on a roll-to-roll scheme using the original board 40. The reflection protective film 110 can be manufactured by such a transfer device 300. The transfer device 300 manufactures the reflection protective film 110 using a photocurable resin. It is a matter of course that the reflection protective film 110 can be manufactured using another kind of curable resin.

The transfer device 300 is equipped with the original board 40, a base material supply roll 301, a winding roll 302, guide rolls 303 and 304, a nip roll 305, a peeling roll 306, an application device 307, and the energy beam source 309.

The base material supply roll 301 is a roll around which a long substrate film 11 has been wound in a roll shape, and the winding roll 302 is a roll around which the reflection protective film 110 is to be wound. The guide rolls 303 and 304 are rolls that transport the substrate film 11. The nip roll 305 is a roll that brings the substrate film 11 on which the uncured resin layer 310 has been laminated, that is, a transfer film 100 in close contact with the original board 40. The peeling roll 306 is a roll that peels the substrate film 11 on which the micro concavo-convex structure 12 has been formed, that is, the reflection protective film 110 from the original board 40.

The application device 307 is equipped with application means such as a coater, applies uncured photocurable resin to the substrate film 11, and forms the uncured resin layer 310. The application device 307 may be a gravure coater, a wire bar coater, a die coater, or the like. The energy beam source 309 is a light source that emits light with a wavelength with which the photocurable resin can be cured and may be an ultraviolet lamp, for example.

First, the substrate film 11 is successively fed from the base material supply roll 301 via the guide roll 303 according to the transfer device 300. The base material supply roll 301 may be changed to a base material supply roll 301 in another lot in the course of the feeding. The application device 307 applies the uncured photocurable resin to the fed substrate film 11, and the uncured resin layer 310 is laminated on the substrate film 11. In this way, the transfer film 100 is manufactured. The transfer film 100 is brought into close contact with the original board 40 by the nip roll 305. The energy beam source 309 cures the uncured resin layer 310 by irradiating the uncured resin layer 310 in close contact with the original board 40 with light. In this way, the micro concavo-convex structure 42 formed on the outer circumferential surface of the original board 40 is transferred to the uncured resin layer 310. That is, the micro concavo-convex structure 12 is formed on the substrate film 11. Subsequently, the substrate film 11 with the micro concavo-convex structure 12 formed thereon, that is, the reflection protective film 110, is peeled from the original board 40 by the peeling roll 306. Then, the reflection protective film 110 is wound by the winding roll 302 via the guide roll 304.

As described above, the transfer device 300 transfers the shape of the outer circumference of the original board 40 to the transfer film 100 while transporting the transfer film 100 in a roll-to-roll manner. In this way, the reflection protective film 110 is manufactured.

When the reflection protective film 110 is manufactured using a thermoplastic resin, the application device 307 and the energy beam source 309 are not needed. Also, the substrate film 11 is formed as a thermoplastic resin film, and a heating device is arranged upstream from the original board 40. The heating device heats and softens the substrate film 11, and the substrate film 11 is then pressed onto the original board 40. In this way, the micro concavo-convex structure 42 formed on the circumferential surface of the original board 40 is transferred to the substrate film 11. The substrate film 11 may be a film formed of a resin other than the thermoplastic resin, and the substrate film 11 and the thermoplastic film may be laminated. In such a case, the laminated film is heated by the heating device and is then pressed onto the original board 40.

Therefore, the transfer device 300 can successively manufacture a transferred article to which the micro concavo-convex structure 42 formed on the original board 40 has been transferred, that is, the reflection protective film 110. Here, the micro concavo-convex structure 42 formed on the circumferential surface of the original board 40 has a desired average period. Therefore, the micro concavo-convex structure 12 formed on the reflection protective film 110 has a desired average period.

<9. Method of Manufacturing Eyeglasses Protection Device>

Next, a method of manufacturing the eyeglasses protection device 1 using the reflection protective film 110 will be described. First, the shape of the eyeglasses protection device 1 is obtained from the reflection protective film 110 by cutting the reflection protective film 110 into the shape of the eyeglasses protection device 1. Then, the eyeglasses protection device 1 is manufactured by forming the attachment parts 3A and 3B in the cut reflection protective film 110. Here, the cutting of the reflection protective film 110 and the formation of the attachment parts 3A and 3B may be performed using a numerically controlled cutting work machine, a laser work machine, a punching press machine, or the like. By using the punching press machine, the cutting of the reflection protective film 110 and the formation of the attachment parts 3A and 3B can be performed in a single process. Therefore, the punching press machine is preferably used to manufacture the eyeglasses protection device 1.

EXAMPLES

Next, examples of the embodiment will be described. In the examples, a plurality of types of eyeglasses protection devices were manufactured by changing the types of the substrate film 11 and the number of surfaces (one surface or both surfaces) on which the micro concavo-convex structure 12 was formed. Then, retardation values of these eyeglasses protection devices with respect to the wavelength of 550 nm, normal reflectance (%), and 3D performance were evaluated.

(Retardation Value)

The retardation values with respect to the measurement wavelength ($\lambda$) of 550 nm were measured using a phase difference measurement device (RETS-100: Otsuka Electronics Co., Ltd.). Here, light with the wavelength of 550 nm is known as light with respect to which a human luminosity factor is the highest. Therefore, retardation values with respect to other wavelengths of visible light are also expected to be low if the retardation value with respect to this light is low.

(Normal Reflectance)

Normal reflection spectroscopic measurement at an incident angle of 5° was performed using an ultraviolet-visible spectrophotometer (V-500: JASCO Corporation), and based on a result thereof, normal reflectance (spectroscopic normal reflectance) at the incident angle of 5° was measured. In the normal reflectance spectroscopic measurement, samples (that is, the eyeglasses protection devices) were directly irradiated with light from a light source. Then, reflected light from the samples was collected by a spherical mirror and was then guided to an integrating sphere. Thereafter, the reflected light was multiply reflected and homogenized in the integrating sphere and was then detected. The normal reflectance is expected to be low at other incident angles when the micro concavo-convex structure 12 is formed on the surface of the lens surface protective part 2.

(3D Performance Evaluation)

The eyeglasses protection devices were attached to associated polarized eyeglasses of a polarization-scheme 3D monitor (D2342P: LG Electronics). Then, the associated polarized eyeglasses (to which the eyeglasses protection device was attached) were put on an observer. Then, a 3D image was displayed on the polarization-scheme 3D monitor, and the observer was shown the 3D image. Then, the observer evaluated quality of the viewed image.

Evaluation criteria for the 3D performance were as follows:

VG (Very Good): No problem in stereoscopic viewing
G (Good): Stereoscopic viewing was possible though crosstalk occurred
B (Bad): Stereoscopic viewing was not possible Example 1

In Example 1, a plate-shaped original board 40 was prepared. The micro concavo-convex structure 42 with an average period of 300 nm was formed on the original board 40. Then, the uncured resin layer 310 was formed by dropping an ultraviolet curable resin (acrylic resin) onto the micro concavo-convex structure 42. Then, a non-stretched polycarbonate film (Technolloy manufactured by Sumitomo Chemical Co., Ltd.) with a thickness of 150 μm was laminated as the substrate film 11 on the uncured resin layer 310. Then, the substrate film 11 was drawn through a rubber roller. Next, the uncured resin layer 310 was completely cured by irradiating the uncured resin layer 310 with ultraviolet rays. In this way, the micro concavo-convex structure 12 was formed on the substrate film 11. That is, the reflection protective film 110 was manufactured. Then, the eyeglasses protection device 1 was manufactured using the reflection protective film 110. Thereafter, a retardation value, normal reflectance, and 3D performance of the eyeglasses protection device 1 were measured and evaluated. The results were that the retardation value was 16 nm and the normal reflectance was 4.7%. In addition, the 3D evaluation result was VG.

Example 2

The same processing as that in Example 1 was performed except that a non-stretched cycloolefin copolymer film (norbornene resin film) (the thickness of 100 μm) was used as the substrate film 11. As a result, the retardation value was 3 nm and the normal reflectance was 4.5%. In addition, the 3D evaluation result was VG.

Example 3

The same processing as that in Example 1 was performed except that the micro concavo-convex structure 12 was formed on both surfaces of the substrate film 11. As a result, the retardation value was 16 nm and the normal reflectance was 0.4%. In addition, the 3D evaluation result was VG.

Example 4

The same processing as that in Example 2 was performed except that the micro concavo-convex structure 12 was formed on both surfaces of the substrate film 11. As a result, the retardation value was 3 nm and the normal reflectance was 0.8%. In addition, the 3D evaluation result was VG.

Example 5

The same processing as that in Example 1 was performed except that a non-stretched polycarbonate film (Iupilon manufactured by Mitsubishi Gas Chemical Company, Inc.) with a thickness of 300 μm was used as the substrate film 11 and the micro concavo-convex structure 12 was formed on both surfaces of the substrate film 11. As a result, the retardation value was 100 nm and the normal reflectance was 0.5%. In addition, the 3D evaluation result was G.

Example 6

The same processing as that in Example 1 was performed except that a stretched polyethylene terephthalate (PET) film (thickness of 125 μm) (Tetoron manufactured by Teijin DuPont Films Japan Limited) with a thickness of 125 μm was used as the substrate film 11. As a result, the retardation value was 5500 nm and the normal reflectance was 5.1%. In addition, the 3D evaluation result was B.

Example 7

The same processing as that in Example 1 was performed except that a stretched polyethylene terephthalate (PET) film (thickness of 100 μm) (Tetoron manufactured by Teijin DuPont Films Japan Limited) with a thickness of 100 μm was used as the substrate film 11. As a result, the retardation value was 5500 nm and the normal reflectance was 0.6%. In addition, the 3D evaluation result was B.

Comparative Example 1

In Comparative Example 1, an eyeglasses protection device was manufactured using the substrate film 11 used in Example 1. As a result, the retardation value was 18 nm and the normal reflectance was 10.9%. In addition, the 3D evaluation result was VG.

Comparative Example 2

In Comparative Example 2, an eyeglasses protection device was manufactured using the substrate film 11 used in Example 2. As a result, the retardation value was 3 nm and the normal reflectance was 8.8%. In addition, the 3D evaluation result was VG.

Comparative Example 3

In Comparative Example 3, an eyeglasses protection device was manufactured using a stretched cycloolefin copolymer film (norbornene resin film) (thickness of 75 μm). As a result, the retardation value was 100 nm and the normal reflectance was 8.8%. In addition, the 3D evaluation result was G.

Comparative Example 4

In Comparative Example 4, an eyeglasses protection device was manufactured using the substrate film 11 used in Example 6. As a result, the retardation value was 5500 nm and the normal reflectance was 11.2%. In addition, the 3D evaluation result was B.

Evaluations of the examples and comparative examples are summarized in Table 1.

TABLE 1

| | Substrate film | Micro concavo-convex structure | Retardation value (nm) | Normal reflectance (%) | 3D performance |
|---|---|---|---|---|---|
| Example 1 | Non-stretched PC | One surface | 16 | 4.7 | VG |
| Example 2 | Non-stretched COC | One surface | 3 | 4.5 | VG |
| Example 3 | Non-stretched PC | Both surfaces | 16 | 0.4 | VG |
| Example 4 | Non-stretched COC | Both surfaces | 3 | 0.8 | VG |
| Example 5 | Non-stretched PC | Both surfaces | 100 | 0.5 | G |
| Example 6 | Stretched PET | One surface | 5500 | 5.1 | B |
| Example 7 | Stretched PET | Both surfaces | 5500 | 0.6 | B |
| Comparative Example 1 | Non-stretched PC | — | 18 | 10.9 | VG |
| Comparative Example 2 | Non-stretched COC | — | 3 | 8.8 | VG |
| Comparative Example 3 | Stretched COC | — | 100 | 8.8 | G |
| Comparative Example 4 | Stretched PET | — | 5500 | 11.2 | B |

As shown in Table 1, it was possible to suppress the normal reflectance to be equal to or less than 5% in Examples 1 to 7. As a result, it was possible to recognize that occurrence of reflected light was able to be suppressed, and glare and eyestrain due to the reflected light were thus able to be reduced in Examples 1 to 7. In particular, it was possible to obtain the normal reflectance that is as significantly small as 1.0% or less by forming the micro concavo-convex structure 12 on both surfaces of the substrate film 11. Therefore, it was possible to recognize that the eyeglasses protection device 1 with the micro concavo-convex structure 12 formed on both surfaces is preferably used in an environment where a shadowless lamp or the like is used.

Furthermore, since the eyeglasses protection devices 1 were manufactured using the non-stretched films as the substrate films 11 in Examples 1 to 5, the retardation values were equal to or less than 100 nm. As a result, the 3D image was able to be viewed without any problems. The satisfactory results of the 3D evaluation were obtained in Examples 1 to 4 in particular, in which the retardation values were equal to or less than 20 nm.

Therefore, it was possible to recognize that the eyeglasses protection device 1 that included the micro concavo-convex structure 12 formed on both surfaces and used the non-stretched film as the substrate film 11 is preferably used when surgery is performed using a shadowless lamp and a 3D endoscopic device.

In contrast, the normal reflectance was significantly high in Comparative Examples 1 to 4. Therefore, it was possible to recognize that the eyeglasses protection devices in Comparative Examples 1 to 4 were not able to sufficiently suppress reflected light.

The preferred embodiment(s) of the present invention has/have been described above with reference to the accompanying drawings, whilst the present invention is not limited to the above examples. A person skilled in the art may find various alterations and modifications within the scope of the appended claims, and it should be understood that they will naturally come under the technical scope of the present invention.

REFERENCE SIGNS LIST 1 eyeglasses protection device
2 lens surface protective part
3 temple protective part
3A, 3B attachment part
11 substrate film
12 micro concavo-convex structure
15, 16, 21, 22 insertion hole
17, 24 auxiliary cut hole
18, 25 auxiliary holding part
20A upper holding part
20B lower holding part

The invention claimed is:
1. An eyeglasses protection device comprising:
a lens surface protective part configured to protect a lens surface of eyeglasses having two ends in a length direction; and
a plurality of temple protective parts that are formed at both ends of the lens surface protective part in the length direction and protect temples of the eyeglasses,
wherein the temple protective parts are equipped with attachment parts equipped with a plurality of insertion holes at which the eyeglasses protection device is configured to be attached to the temples of the eyeglasses,
wherein the lens surface protective part is equipped with a substrate film,
wherein the plurality of insertion holes are entirely separated from each other by the substrate film,
wherein the plurality of insertion holes extend substantially parallel to each other,
wherein the plurality of insertion holes each comprise one end and another end,
wherein the attachment parts are equipped with one or a plurality of auxiliary cut holes that extend from a position between the one end of the insertion holes and the another end of the insertion holes, and
wherein a micro concavo-convex structure is formed on a surface of the substrate film, with an average period of the micro concavo-convex structure being in a range equal to or less than 830 nm.

2. The eyeglasses protection device according to claim 1, wherein the temples of the eyeglasses are configured to be inserted into the plurality of insertion holes, and
wherein the plurality of insertion holes are aligned in an insertion direction of the temples.

3. The eyeglasses protection device according to claim 2, wherein the attachment parts are equipped with
a traverse cut hole that crosses in an oblique direction between adjacent insertion holes of the plurality of insertion holes, and
an upper holding part and a lower holding part formed by the plurality of insertion holes and the traverse cut hole.

4. The eyeglasses protection device according to claim 3, wherein the traverse cut hole is formed at one temple protective part among the plurality of temple protective parts.

5. The eyeglasses protection device according to claim 3, wherein the traverse cut hole crosses between the one end of one insertion hole of the adjacent insertion holes and the another end of another insertion hole of the adjacent insertion holes.

6. The eyeglasses protection device according to claim 2, wherein the one or the plurality of auxiliary cut holes extend from outer edges of the insertion holes toward outside of the insertion holes, and
wherein the attachment parts are equipped with auxiliary holding parts formed by the auxiliary cut holes in circumferences of the insertion holes.

7. The eyeglasses protection device according to claim 6, wherein the one or the plurality of auxiliary cut holes of one insertion hole of the plurality of insertion holes are entirely separated from other insertion holes of the plurality of insertion holes by the substrate film.

8. The eyeglasses protection device according to claim 1, wherein the micro concavo-convex structure is formed of a hardened ultraviolet curable resin.

9. The eyeglasses protection device according to claim 1, wherein the micro concavo-convex structure comprises a compound that includes a hydrophilic functional group.

10. The eyeglasses protection device according to claim 1, wherein an in-plane retardation value of the lens surface protective part is equal to or less than 100 nm with respect to a wavelength of visible light, and
wherein the substrate film is made of a non-stretched film.

11. An eyeglasses protection device laminated article in which the eyeglasses protection device according to claim 1 is laminated.

12. The eyeglasses protection device according to claim 1, wherein the one or the plurality of auxiliary cut holes extend in a direction perpendicular to a length of the insertion holes.

13. The eyeglasses protection device according to claim 1, wherein the one or the plurality of auxiliary cut holes extend, from outer edges of adjacent insertion holes of the plurality of insertion holes of one temple protective part of the plurality of temple protective parts, toward outside of the adjacent insertion holes of the one temple protective part, and
wherein the one or the plurality of auxiliary cut holes extend, from inner edges of adjacent insertion holes of the plurality of insertion holes of another temple protective part of the plurality of temple protective parts, toward inside of the adjacent insertion holes of the another temple protective part.

14. An eyeglasses protection device comprising:
a lens surface protective part configured to protect a lens surface of eyeglasses having two ends in a length direction; and
a plurality of temple protective parts that are formed at both ends of the lens surface protective part in the length direction and protect temples of the eyeglasses,
wherein the temple protective parts are equipped with attachment parts equipped with a plurality of insertion holes at which the eyeglasses protection device is configured to be attached to the temples of the eyeglasses, wherein the lens surface protective part is equipped with a substrate film, wherein the plurality of insertion holes are entirely separated from each other by the substrate film, wherein the plurality of insertion holes extend substantially parallel to each other, wherein the temples of the eyeglasses are configured to be inserted into the plurality of insertion holes, wherein the plurality of insertion holes are aligned in an insertion direction of the temples, wherein the attachment parts are equipped with
- a traverse cut hole that crosses in an oblique direction between adjacent insertion holes of the plurality of insertion holes, and
- an upper holding part and a lower holding part formed by the plurality of insertion holes and the traverse cut hole, and wherein a micro concavo-convex structure is formed on a surface of the substrate film, with an average period of the micro concavo-convex structure being in a range equal to or less than 830 nm.

15. The eyeglasses protection device according to claim 14, wherein the traverse cut hole is formed at one temple protective part among the plurality of temple protective parts.

16. The eyeglasses protection device according to claim 14, wherein the insertion holes each comprise one end and another end, and wherein the traverse cut hole crosses between the one end of one insertion hole of the adjacent insertion holes and the another end of another insertion hole of the adjacent insertion holes.

* * * * *